US010078090B2

(12) United States Patent
Chambers

(10) Patent No.: US 10,078,090 B2
(45) Date of Patent: Sep. 18, 2018

(54) SAB AS A BIOMARKER FOR DEGENERATIVE DISEASES AND THERAPEUTIC SENSITIVITY IN CANCERS

(71) Applicant: Jeremy W. Chambers, Miramar, FL (US)

(72) Inventor: Jeremy W. Chambers, Miramar, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/828,842

(22) Filed: Dec. 1, 2017

(65) Prior Publication Data

US 2018/0080944 A1 Mar. 22, 2018

Related U.S. Application Data

(63) Continuation of application No. 14/805,022, filed on Jul. 21, 2015.

(60) Provisional application No. 62/026,894, filed on Jul. 21, 2014.

(51) Int. Cl.
| | | |
|---|---|---|
| *G01N 33/68* | (2006.01) | |
| *G01N 33/574* | (2006.01) | |
| *A61K 31/337* | (2006.01) | |
| *A61K 31/519* | (2006.01) | |
| *A61K 31/69* | (2006.01) | |
| *A61K 31/167* | (2006.01) | |
| *A61K 31/5377* | (2006.01) | |
| *C12Q 1/6883* | (2018.01) | |
| *A61K 38/07* | (2006.01) | |
| *C07K 16/28* | (2006.01) | |
| *G01N 33/50* | (2006.01) | |
| *C12Q 1/6886* | (2018.01) | |
| *C07K 16/18* | (2006.01) | |

(52) U.S. Cl.
CPC ....... *G01N 33/6893* (2013.01); *A61K 31/167* (2013.01); *A61K 31/519* (2013.01); *A61K 31/5377* (2013.01); *A61K 31/69* (2013.01); *A61K 38/07* (2013.01); *C07K 16/18* (2013.01); *C07K 16/2878* (2013.01); *C07K 16/2887* (2013.01); *C12Q 1/6883* (2013.01); *C12Q 1/6886* (2013.01); *G01N 33/5079* (2013.01); *G01N 33/574* (2013.01); *G01N 33/6872* (2013.01); *C07K 2317/24* (2013.01); *C12N 2710/10043* (2013.01); *C12N 2750/14143* (2013.01); *C12Q 2600/106* (2013.01); *C12Q 2600/118* (2013.01); *C12Q 2600/136* (2013.01); *C12Q 2600/158* (2013.01); *G01N 2500/10* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 4,894,348 A | 1/1990 | Ronald et al. | |
|---|---|---|---|
| 2006/0281122 A1* | 12/2006 | Bryant | C12Q 1/6886 435/6.16 |
| 2009/0280510 A1* | 11/2009 | Cardone | C07K 16/18 435/7.21 |
| 2010/0311084 A1* | 12/2010 | Brower | G01N 33/5091 435/7.23 |
| 2011/0183336 A1* | 7/2011 | Gray | C12Q 1/6886 435/6.12 |

FOREIGN PATENT DOCUMENTS

| WO | WO-2004038020 A1 * | 5/2004 | ............. C07K 14/47 |
|---|---|---|---|
| WO | 2012044696 A2 | 4/2012 | |

OTHER PUBLICATIONS

Wiltshire et al. Biochemical Society Transactions, 32(6): 1075-1077). (Year: 2004).*
Bruning et al., Current Cancer Drug Targets, 11(7):799-809). (Year: 2011).*
Chambers, Jeremy W. et al., "Selective Inhibition of Mitochondrial JNK Signaling Achieved Using Peptide Mimicry of the Sab Kinase Interacting Motif-1 (KIM1)," ACS Chem. Biol., Aug. 2011, 6(8):808-818.
Chambers, Jeremy W. et al., "Inhibition of JNK Mitochondrial Localization and Signaling Is Protective against Ischemia/Reperfusion Injury in Rats." The Journal of Biological Chemistry, Feb. 2013, 288(6): 4000-4011.
Court, Naomi W. et al., "Phosphorylation of the mitochondrial protein Sab by stress-activated protein kinase 3," Biochemical and Biophysical Research Communications, 2004, 319:130-137.
Matsushita, Masato et al., "Identification and Characterization of a Novel SH3-Domain Binding Protein, Sab, Which Preferentially (Continued)

*Primary Examiner* — Hong Sang
(74) *Attorney, Agent, or Firm* — Saliwanchik, Lloyd & Eisenschenk

(57) ABSTRACT

The current invention pertains to a method of diagnosing a disease or identifying an increased likelihood of developing the disease in a subject. The method comprises determining the level of Src homology 3 domain binding protein 5 (SH3BP5 or SAB) or the RNA encoding SAB protein in a biological sample obtained from the subject and identifying the subject as having the disease or having an increased likelihood of developing the disease if the biological sample obtained from the subject has an altered level of SAB protein or the RNA encoding SAB protein relative to a control sample. The methods of the current invention can be practiced to diagnose and treat a systemic degenerative disease, a neurodegenerative disease, obesity, diabetes, a cancer, or an aging related disease. The invention also provides a kit for diagnosing a disease or diagnosing an increased likelihood of developing the disease in a subject.

16 Claims, 17 Drawing Sheets

Specification includes a Sequence Listing.

(56) References Cited

OTHER PUBLICATIONS

Associates with Bruton's Tyrosine Kinase (Btk)," Biochemical and Biophysical Research Communications, 1998, 245:337-343.
Stratagene Catalog, 1988, p. 39.
Takeshita, Y., et al., "SH3-binding Protein 5 Mediates the Neuroprotective Effect of the Secreted Bioactive Peptide Humanin by Inhibiting c-Jun NH2-terminal Kinase." The Journal of Biological Chemistry, Aug. 2013, 288(34): 24691-24704.
Wiltshire, Carolyn et al., "A new c-Jun N-terminal kinase (JNK)-interacting protein, Sab (SH3BP5), associates with mitochondria," Biochem. J., 2002, 367:577-585.
Yamadori, Tomoki et al., "Bruton's tyrosine kinase activity is negatively regulated by Sab, the Btk-SH3 domain-binding protein," Proc. Natl. Acad. Sci. USA, Immunology, May 1999, 96:6341-6346.

\* cited by examiner

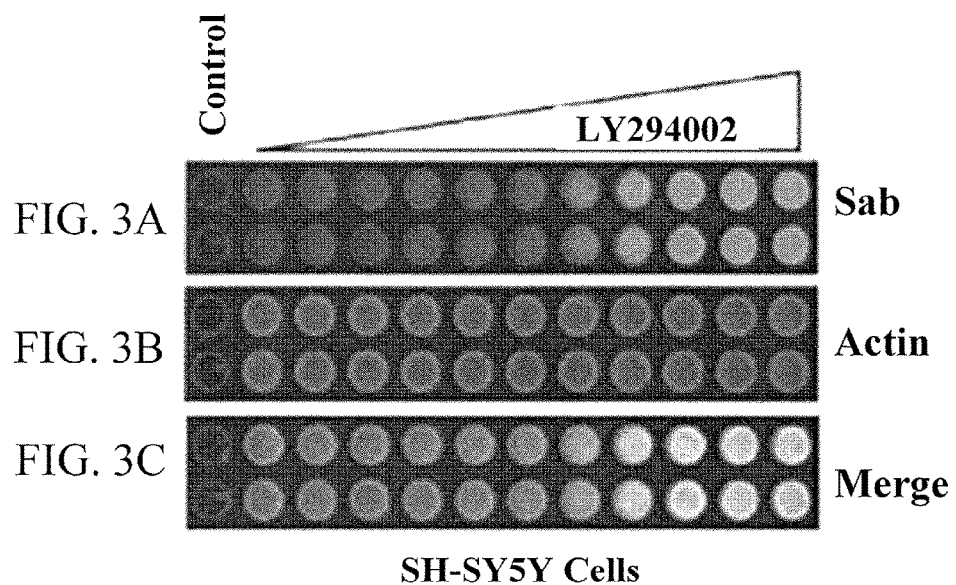
FIG. 3A
FIG. 3B
FIG. 3C
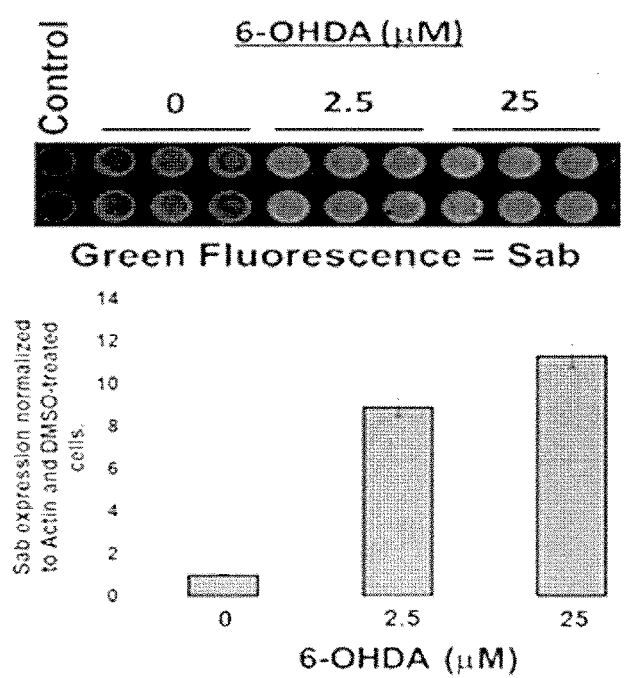
FIG. 4

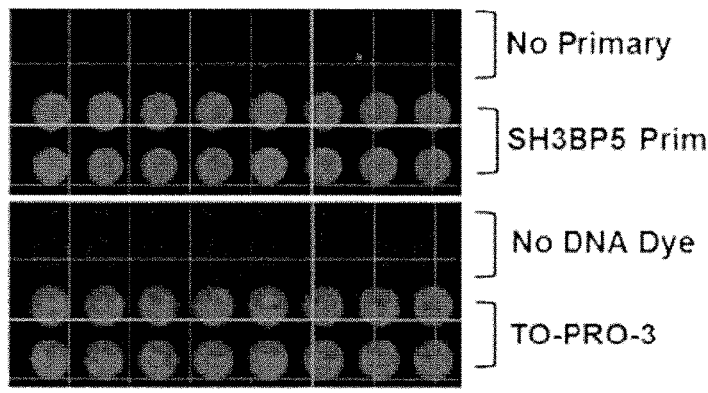
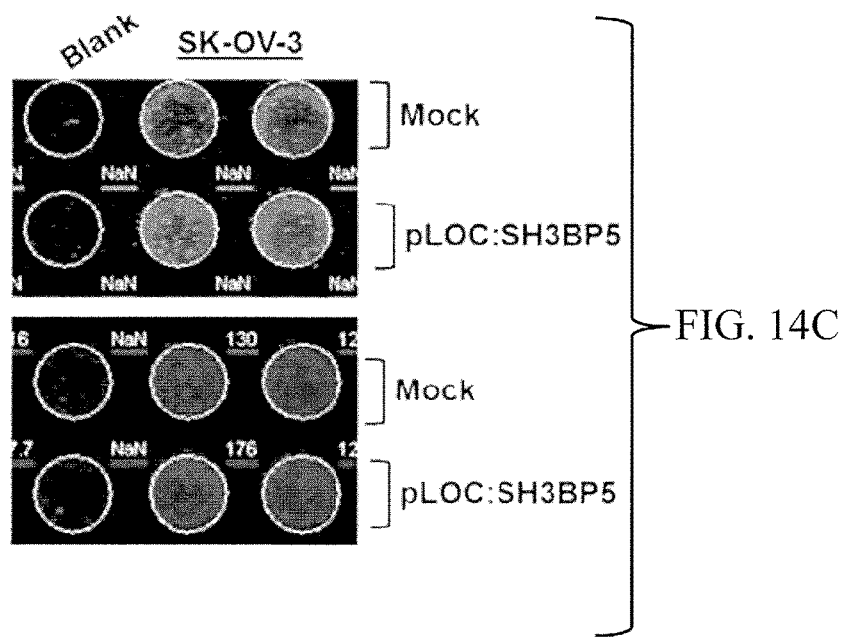
FIG. 14A
FIG. 14B
FIG. 14C

SAB AS A BIOMARKER FOR DEGENERATIVE DISEASES AND THERAPEUTIC SENSITIVITY IN CANCERS

CROSS REFERENCE TO RELATED APPLICATION(S)

This application is a continuation of U.S. application Ser. No. 14/805,022, filed Jul. 21, 2015, which claims the benefit of U.S. Provisional Application Ser. No. 62/026,894, filed Jul. 21, 2014, which are hereby incorporated by reference in their entirety, including any figures, tables, or drawings.

The Sequence Listing for this application is labeled "SEQ-LIST-07-21-15-ST25.txt", which was created on Jul. 21, 2015, and is 2 KB. The entire content is incorporated herein by reference in its entirety.

BACKGROUND OF INVENTION

The current technology for diagnosing degenerative diseases focuses on blood factors that are commonly associated with normal immune responses. Since these blood factors are associated with normal immune responses, such biomarkers do not provide an accurate prediction of the occurrence of degenerative diseases. Therefore, there is a need for a more specific biomarker for diagnosis of degenerative diseases.

The protein Src homology 3 binding protein 5 (SH3BP5 or SAB) is a scaffold protein found on the outer mitochondrial membrane of mammalian cells. SAB coordinates signaling components on the outer mitochondrial membrane; these components can drive processes such as mitochondrial dysfunction and cell death. For example, increased level of SAB in a cell indicates a significant amount of mitochondrial damage in the cell. Significant mitochondrial damage in a cell ultimately leads to cell death. SAB protein is also implicated in the pathophysiology associated with Parkinson's disease, acetaminophen toxicity, heart attack, and ischemic injury.

SAB acts early during degenerative diseases to prepare the cell for cell death which leads to tissue damage later in the progression of the disease. The mechanism of cell death and tissue loss may involve SAB organizing the signaling components that destabilize the integrity of the mitochondrial membrane and membrane potential. This destabilization may reduce metabolic efficiency and recruit death inducing proteins to the mitochondrial surface. SAB levels also change in response to chronic stress associated with a number of degenerative conditions.

Accurate identification of cancers susceptible to apoptosis inducing chemotherapies or radiation therapies is of great importance when physicians evaluate treatment options for their patients. Therefore, a need exists to identify factors within tumors that may indicate a cancer's vulnerability to current chemotherapeutic approaches. Using SAB as a biomarker for primed mitochondria, one can identify cancers with early-primed mitochondria as being amenable to treatment via chemotherapy.

BRIEF SUMMARY

The subject invention provides materials and methods for monitoring and modulating mitochondrial function. Specifically, in accordance with the subject invention, Src homology 3 domain binding protein 5 (SH3BP5 or SAB) has been found to coordinate signaling components on the outer mitochondrial membrane. These components can drive processes involved in mitochondrial dysfunction and cell death. Specifically, these signaling components destabilize the integrity of the mitochondrial membrane potential thereby reducing metabolic efficiency, which can lead to the recruitment of death-inducing proteins to the mitochondrial surface.

In accordance with the subject invention, SAB levels and/or activity can be monitored in order to evaluate the status and/or development of conditions including aging, degenerative diseases (including cognitive degenerative diseases), obesity, and growth inhibition.

The subject invention further provides methods of treatment for these conditions wherein the methods of treatment include modulating the levels and/or activity of the SAB protein.

The subject invention further provides methods of promoting cell death for cells, such as autoimmune cells, that have deleterious effects on health.

In certain specific embodiments, the current invention provides assays for the detection and/or monitoring of human degenerative diseases. Advantageously, these assays can be used for early detection of degenerative diseases and they provide a faster and less expensive method for diagnosing degenerative diseases.

In another embodiment of the current invention, SAB protein can be used as an indicator of cancer cells that are susceptible to treatment with apoptosis-inducing chemotherapeutic agents and/or radiation. Using SAB as a biomarker for cancer susceptibility not only facilitates early detection of cancer but also provides a method for identifying methods of cancer treatment.

In one embodiment, the method of the subject invention comprises the steps of:

a) determining the level of SAB protein or the RNA encoding SAB protein in a biological sample obtained from a subject;

b) determining the level of SAB protein, or the RNA encoding SAB protein, in a control sample;

c) identifying the subject as having the disease or having an increased likelihood of developing the disease compared to an individual known to have a low likelihood of developing the disease if the biological sample obtained from the subject has an altered level of SAB protein or the RNA encoding SAB protein relative to the level of SAB protein or RNA encoding SAB protein in the control sample; and, optionally, d) selecting a treatment for the disease for the subject identified as having the disease or having an increased likelihood of developing the disease; and, optionally, e) administering the treatment to the subject identified as having the disease or having an increased likelihood of developing the disease.

The methods of the current invention can be practiced to diagnose and treat a disease selected from, for example, systemic degenerative diseases, neurodegenerative diseases, obesity, diabetes, cancer, and aging related diseases.

The biological sample and/or the control sample in which the level of SAB protein or RNA encoding SAB protein is determined can be, for example, a tissue sample, or a body fluid sample.

In accordance with the present invention it has been determined that elevated levels of SAB on mitochondria represent a population of early primed mitochondria in cancer cells susceptible to killing by apoptosis-inducing chemotherapies and/or radiation therapies. Accordingly, SAB represents a novel biomarker of cancer cells that are susceptible to treatment with apoptosis-inducing chemotherapy.

The invention also provides kits for diagnosing a disease or diagnosing an increased likelihood of developing the disease in a subject. The kit can comprise an agent that specifically binds to SAB protein, or to RNA encoding SAB protein, that can optionally be labeled, that facilitates the determination of the level of SAB protein or RNA encoding SAB protein. The kit can further comprise a second agent that binds to the binding agent, wherein the second agent is labeled to facilitate the determination of the level of SAB protein, or RNA encoding SAB protein in the sample. Additionally, the kit can comprise reagents for preparation of biological samples, reagents for preparation of reaction mixtures, washing reagents, and reagents for visualization of the binding between the agent and the SAB protein or RNA encoding SAB protein.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings.

This patent or application file contains at least one drawing executed in color. Copies of this patent or patent application publication, with color drawing(s), will be provided by the Office upon request and payment of the necessary fee.

FIGS. 3A-3C show in-cell western for SAB-expression in SH-SY5Y cells.

FIG. 4 shows in-cell western for SAB-expression in SH-SY5Y cells treated with sub-chronic doses of 6-OHDA.

FIGS. 14A-14C show that SH3BP5 expression can be detected using an in-cell western assay.

BRIEF DESCRIPTION OF SEQUENCES

Figure 1:
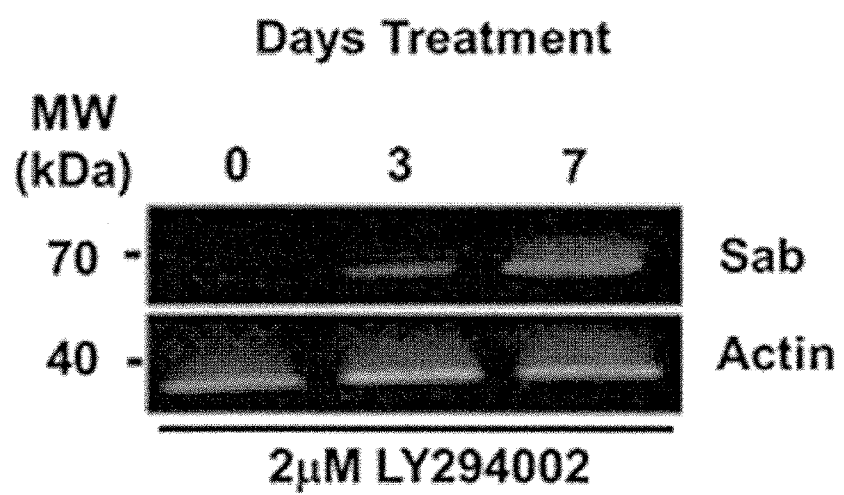
FIG. 1 shows SAB-expression increases during LY294002 sensitization of HeLa cells.

SEQ ID NO: 1: Sense oligonucleotide for KIM1 mutagenesis.

SEQ ID NO: 2: Anti-sense oligonucleotide for KIM1 mutagenesis.

SEQ ID NO: 3: Sense oligonucleotide for KIM2 mutagenesis.

SEQ ID NO: 4: Anti-sense oligonucleotide for KIM2 mutagenesis.

SEQ ID NO: 5: shRNA to inhibit Sab expression.

SEQ ID NO: 6: Sense oligonucleotide for introducing silent mutations in Sab expression constructs.

SEQ ID NO: 7: Anti-sense oligonucleotide for introducing silent mutations in Sab expression constructs.

DETAILED DISCLOSURE

The current invention provides new assays for the detection and/or monitoring of human degenerative diseases. Advantageously, in certain embodiments these assays can be used for early detection of degenerative diseases. These assays also provide a faster and less expensive method for diagnosing degenerative diseases.

In a further embodiment of the current invention, SAB protein can be used as an indicator of cancer that is susceptible to treatment with apoptosis-inducing chemotherapeutic agents and/or radiation.

SAB protein is expressed in several mammals and a person of ordinary skill in the art can obtain the amino acid sequence of SAB protein and the nucleotide sequences of mRNA and DNA in a particular mammal from, for example, the NCBI website. A person of ordinary skill in the art can also obtain information about various homologs and splice variants of SAB protein. The following table (Table 1) provides NCBI accession numbers of certain SAB protein, mRNA, and DNA from several mammals.

TABLE 1

NCBI accession numbers of SAB protein, mRNA, and DNA in mammals.

| Organism | Protein (GenBank accession number) | mRNA (GenBank accession number) | DNA (Gene ID) |
|---|---|---|---|
| Humans | O60239 | NM_004844 | 9467 |
| Mouse | Q9Z131 | NM_001161338.1 | 24056 |
| Rat | NP_446463 | BC166447.1 | 117186 |
| Pig | XP_003132111 | XM_003123598.4 | 100517856 |
| Cow | NP_001193217 | NM_001075802.1 | 618056 |
| Cat | XP_003992178 | XM_003992129.2 | 101092392 |
| Dog | XP_005634458 | XM_005634401.1 | 485657 |

Using SAB as a biomarker for cancer susceptibility not only facilitates early detection of cancer but also provides a method for identifying methods of cancer treatment.

One embodiment of the current invention provides a method of diagnosing a disease or identifying an increased likelihood of developing the disease in a subject, and treating or preventing the disease in the subject. The method comprises the steps of:

a) determining the level of SAB protein or the RNA encoding SAB protein in a biological sample obtained from the subject;

b) determining the level of SAB protein or the RNA encoding SAB protein in a control sample;

c) identifying the subject as having the disease or having an increased likelihood of developing the disease compared to an individual known to have a low likelihood of developing the disease if the biological sample obtained from the subject has an altered level of SAB protein or the RNA encoding SAB protein relative to the level of SAB protein or the RNA encoding SAB protein in the control sample; and, optionally, d) selecting a treatment for the disease for the subject identified as having the disease or having an increased likelihood of developing the disease; and, optionally, e) administering the treatment to the subject identified as having the disease or having an increased likelihood of developing the disease.

The term "treatment of a disease" or any grammatical variation thereof (e.g., treat, treating, and treatment etc.), as used herein, includes, but is not limited to, ameliorating or alleviating a symptom of the disease; reducing or delaying recurrence of the disease; and/or reducing, suppressing, inhibiting, lessening, or affecting the progression and/or severity of undesired physiological changes associated with the disease. Complete remission of the disease is not required for a treatment of the disease according to the current invention.

Also, the term "treatment of a cancer" or any grammatical variation thereof includes inhibiting, or slowing the rate of development of cancer or conversion of a benign cancerous cell, tissue, or tumor into a malignant cell, tissue, or tumor; slowing the growth and/or proliferation of cancer; and reducing the size of cancerous tumor. Complete remission of the cancer is not required for a treatment of a cancer according to the current invention.

The term "prevention" as used herein refers to a measure or procedure performed to prevent rather than to treat or cure a disease. Accordingly, prevention includes, but is not limited to, delaying the onset of symptoms, preventing relapse to a disease, or a combination thereof. Prevention as used herein does not require the complete absence of the disease or its symptoms.

The method of the current invention can be practiced for diagnosis and treatment of a disease in a mammal. Non-limiting examples of mammals in which the current invention can be practiced include humans, non-human primates, pigs, bovines, felines, and canines. Additional examples of mammals in which the methods of the current invention can be practiced are well known to a person of ordinary skill in the art and such embodiments are within the purview of the current invention.

In certain embodiments of the current invention, the method of the current invention is practiced to diagnose a disease and/or identify an increased likelihood of developing the disease, wherein the disease is selected from systemic degenerative diseases, neurodegenerative diseases, obesity, diabetes, cancer, and aging related diseases.

For the purpose of the current invention a systemic disease refers to a disease that affects a plurality of organs and tissues, or affects the body as a whole. Also, for the purpose of the current invention, a degenerative disease refers to a disease in which the function and/or structure of an affected tissue or organ deteriorates or degenerates over time, including death of cells in the organ. Accordingly, a systemic degenerative disease is a disease in which the function and/or structure of a plurality of organs and tissues or the body as a whole deteriorates or degenerates over time.

According to the current invention, if the level of SAB protein, or the RNA encoding SAB protein, in a biological sample obtained from a subject is increased relative to the level of SAB protein, or the RNA encoding SAB protein, in a control sample, the subject is identified as having the systemic degenerative disease or having an increased likelihood of developing the systemic degenerative disease compared to an individual having a low likelihood of developing the systemic degenerative disease.

Non-limiting examples of systemic degenerative diseases that can be diagnosed according to the methods of the current invention include muscular dystrophy, muscular atrophy, cancer, multiple systems atrophy, multiple sclerosis, atherosclerosis, degenerative heart disease, diabetes, inflammatory bowel disease, osteoarthritis, rhematoid arthritis, chronic obstructive pulmonary disease, prostatitis, osteoporosis, and keratoconus.

In certain other embodiments of the invention, the method of the current invention is practiced to diagnose a neurodegenerative disease. For the purpose of the current invention, a neurodegenerative disease refers to a disease in which function and/or structure of the nervous system deteriorates or degenerates over time including death of nerve cells. Non-limiting examples of neurodegenerative diseases that can be diagnosed according to the methods of the current invention include Parkinson's disease, Alzheimer's disease, Huntington's disease, amyotrophic lateral sclerosis, Friedreich's ataxia, Niemann Pick disease, progressive supranuclear palsy, and essential tremor.

According to the current invention, if the level of SAB protein, or the RNA encoding SAB protein, in a biological sample obtained from a subject is increased relative to the level of SAB protein, or the RNA encoding SAB protein, in a control sample, the subject is identified as having the neurodegenerative disease or having an increased likelihood of developing the neurodegenerative disease compared to an individual having a low likelihood of developing the neurodegenerative disease. A biological sample obtained from a nerve tissue, for example, brain, spinal cord, or cerebrospinal fluid, can be used to diagnose the neurodegenerative disease or identify an increased likelihood of developing the neurodegenerative disease.

In one embodiment, the method of the current invention is used to diagnose a cancer. In a further embodiment, the method is used to diagnose a cancer that is susceptible to treatment using apoptosis-inducing chemotherapeutic agents and/or radiation.

According to the current invention, if the level of SAB protein, or the RNA encoding SAB protein, in a biological sample obtained from the subject is increased relative to the level of SAB protein, or the RNA encoding SAB protein, in the control sample, the subject is identified as having a cancer or having an increased likelihood of developing a cancer compared to an individual having a low likelihood of developing the cancer, wherein the cancer is susceptible to treatment using apoptosis-inducing chemotherapeutic agents and/or radiation treatments.

For the purpose of this invention, apoptosis-inducing chemotherapeutic drug and/or radiation treatment refers to cancer treatment by chemical and/or radiation that induces apoptosis in cancer cells, thereby treating cancer. Non-limiting examples of apoptosis-inducing cancer chemotherapeutic agents include docetaxel, 6-mercaptopurine, Cisplatin, Vorinostat (Zolinza™), Romidepsin (Istodax™), Bortezomib (Velcade™), Carfilzomib (Kyprolis™), Pralatrexate (Folotyn™), Rituximab (Rituxan™), and Brentuximab vedotin (Adcetris™).

In certain embodiments, the methods of the current invention are practiced to diagnose or identify an increased risk of developing a cancer, wherein the cancer is selected from leukemia, bladder cancer, bone cancer, brain tumor, central nervous system tumors, brain and spinal cord tumors, breast cancer, bronchial tumors, Burkitt lymphoma, gastrointestinal cancer, cervical cancer, colorectal cancer, esophageal cancer, head and neck cancer, liver cancer, Hodgkin lymphoma, islet cell tumors (endocrine pancreas), Kaposi sarcoma, kidney cancer, laryngeal cancer, lip and oral cavity cancer, lung cancer, non-small cell lung cancer, small cell lymphoma, AIDS-related lymphoma, Burkitt lymphoma, cutaneous T-cell lymphoma, non-Hodgkin lymphoma, ovarian cancer, testicular cancer, and vaginal cancer.

In one embodiment of the invention, the method of the current invention is practiced to diagnose an aging related disease. Non-limiting examples of aging related diseases that can be diagnosed according to the methods of current invention include sarcopenia, frailty, fatiguability, and cognitive decline.

According to the current invention, if the level of SAB protein, or the RNA encoding SAB protein, in a biological sample obtained from the subject is increased relative to the level of SAB protein, or the RNA encoding SAB protein, in a control sample, the subject is identified as having the aging related disease or having an increased likelihood of developing the aging related disease compared to an individual having a low likelihood of developing an aging related disease or a young individual.

In a further embodiment of the invention, the method of the current invention is practiced to diagnose growth inhibition in a subject. According to the current invention, if the level of SAB protein, or the RNA encoding SAB protein, in a biological sample obtained from the subject is reduced relative to the level of SAB protein, or the RNA encoding SAB protein, in a control sample, the subject is identified as having growth inhibition or having an increased likelihood of developing growth inhibition compared to an individual having a low likelihood of developing growth inhibition.

In certain embodiments of the invention, the biological sample and/or the control sample in which the level of SAB protein, or RNA encoding SAB protein, is determined is a tissue sample. Non-limiting examples of tissue samples that can be used to practice the methods of the current invention include blood, brain, eyes, pineal gland, pituitary gland, thyroid gland, parathyroid glands, thorax, heart, lungs, esophagus, thymus gland, pleura, Adrenal gland, appendix, gall bladder, urinary bladder, large intestine, small intestine, kidneys, liver, pancrease, spleen, stoma, prostate gland, testes, ovaries, uterus, muscle, adipose, and nerve.

In further embodiments of the invention, the biological sample and/or the control sample in which the level of SAB protein or RNA encoding SAB protein is determined is a body fluid sample. Non-limiting examples of body fluid samples that can be used to practice the methods of the current invention include aqueous humour, vitreous humour, bile, urine, blood serum, blood plasma, cerebrospinal fluid, endolymph, perilymph, exudates, lymph, mucus, pericardial fluid, pleural fluid, and synovial fluid.

The control sample used to diagnose the presence of a disease in a subject or to identify an increased risk of developing the disease in the subject can be:

a) a sample obtained from an individual known to be free from the disease or known to have a low likelihood of developing the disease, b) a sample obtained from the subject when the subject was known to be free from the disease or was known to have a low likelihood of developing the disease, or c) a sample containing SAB protein or fragment thereof, or RNA encoding SAB protein or a fragment thereof at a maximum level known that indicates the absence of the disease or a low likelihood of developing the disease.

In one embodiment of the invention, the control sample used in the methods of the current invention is obtained from an individual known to be free from the disease or known to have a low likelihood of developing the disease. In another embodiment of the invention, multiple samples from multiple individuals known to be free from the disease or known to have a low likelihood of developing the disease are used to provide multiple points of reference.

In one embodiment of the invention, the control sample used in the methods of the current invention is obtained from the subject when the subject was known to be free from the disease or was known to have a low likelihood of developing the disease. Samples from the subject when the subject was known to be free from the disease or was known to have a low likelihood of developing the disease can be collected and preserved for later use. In another embodiment of the invention, multiple samples obtained from the subject at different time points when the subject was known to be free from the disease or was known to have a low likelihood of developing the disease can be collected and preserved and later used to provide multiple points of reference.

In one embodiment of the invention, the control sample used in the methods of the current invention is a sample containing SAB protein or a fragment thereof, or RNA encoding SAB protein or a fragment thereof, at a maximum level known to indicate the absence of the disease or a low likelihood of developing the disease. In one embodiment of the invention, a control sample is a solution or a composition containing a known concentration of SAB protein or a fragment thereof. In a further embodiment of the invention, a control sample is a solution or a composition containing a known concentration of RNA encoding SAB protein or a fragment thereof.

The SAB fragment may be, for example, at least 50%, 75%, 80%, 85%, 90%, 95%, or 99% the length of the full-length SAB protein.

The maximum concentration of SAB protein or a fragment thereof, or RNA encoding SAB protein or a fragment thereof that indicates the absence of a disease or indicates an increased likelihood of developing the disease is determined by determining the level of SAB protein or RNA encoding SAB protein in a large number of samples obtained from individuals known to be free from the disease or known to have a low likelihood of developing the disease and comparing the levels of SAB protein or RNA encoding SAB protein in these samples with the corresponding values obtained for samples from individuals known to have the disease or known to have an increased likelihood of developing the disease.

For example, if concentrations of SAB protein in all samples obtained from individuals known to be free from the disease or known to have a low likelihood of developing the disease are lower than a particular concentration and the concentrations of SAB protein in all samples obtained from individuals known to have the disease or known to have an increased likelihood of developing the disease are higher than the particular concentration, a solution or a composition containing the particular concentration of SAB protein can be used as a control sample. Alternatively, this particular concentration can be used as a reference value to determine the presence of a disease in a subject or increased likelihood of developing the disease in the subject without running a control sample.

Various methods can be used to determine the level of SAB protein, or RNA encoding SAB protein, in the biological samples. For example, the level of SAB protein can be determined by immublotting, immunoprecipitation, immunofluorescence, immunostaining, immunoelectrophoresis, or enzyme-linked immunosorbent assay (ELISA). Additional methods of determining the level of SAB protein in biological samples are well known to a person of ordinary skill in the art and such methods are within the purview of the current invention.

The level of RNA encoding SAB protein can be determined by northern blotting, reverse-transcription polymerase chain reaction, quantitative polymerase chain reaction or real time polymerase chain reaction, and ribonuclease protection assay. Additional methods of determining the level of RNA encoding SAB protein are well known to a person of ordinary skill in the art and such methods are within the purview of the current invention.

The current invention also provides methods of selecting a treatment for a disease if the subject is identified as having the disease. The current invention also provides methods of selecting a treatment for preventing the occurrence of the disease if the subject is identified as having an increased likelihood of developing the disease. The current invention can also further comprise administering the treatment for the disease to the subject identified as having the disease or administering the treatment for preventing the occurrence of the disease to the subject identified as having an increased likelihood of developing the disease.

Treatments for various diseases described herein are well known to a person of ordinary skill in the art and one can select an appropriate treatment for a subject. For example, one can select a treatment for a subject based on the disease, the severity of the disease, the age of the subject, and other relevant aspects of the subject that can affect the treatment options.

A further embodiment of the invention provides a kit for diagnosing a disease or diagnosing an increased likelihood of developing the disease in a subject. The kit can, for example, comprise an agent that specifically binds to SAB protein or RNA encoding SAB protein.

For the purpose of this invention, "specific binding" refers to the binding between an agent and SAB protein or RNA encoding SAB protein that is based on specific interactions between sites present on the agent and SAB protein or RNA encoding SAB protein. On the other hand, "non-specific binding" refers to the binding that is not based on specific interactions between a molecule and the SAB protein or RNA encoding SAB protein.

Non-limiting examples of agents that can specifically bind to SAB protein include antibodies against SAB protein, a fragment of an antibody against SAB protein, and an aptamer specifically binding to SAB protein. Additional examples of agents capable of specifically binding to SAB protein are well known to a person of ordinary skill in the art and such embodiments are within the purview of the current invention.

Non-limiting examples of agents that can specifically bind to RNA encoding SAB protein include polynucleotide probes having a high degree of sequence complementarity with the nucleotide sequence of RNA encoding SAB protein or a fragment thereof. In certain embodiments of the invention, the agent that can specifically bind to RNA encoding SAB protein has at least about 70%, about 75%, about 80% about 95%, or about 98% sequence complementarity to the nucleotide sequence of RNA encoding SAB protein or a fragment thereof.

The specific binding affinity between an agent and RNA encoding SAB protein depends on the sequence complementarity between the binding agent and the RNA encoding SAB protein and the conditions of hybridization. For example, higher sequence complementarity is required for specific binding between the agent and the RNA under conditions of high stringency; whereas, lower sequence complementarity can be sufficient for specific binding between the agent and the RNA under conditions of lower stringency. A person of ordinary skill in the art can modulate the specific binding between the agent and the RNA by altering the sequence complementarity and/or the stringency of the hybridization conditions and such embodiments are within the purview of the current invention.

Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak [1987] *DNA Probes*, Stockton Press, New York, N.Y., pp. 169-170.

Examples of conditions that can be employed for high and intermediate stringency are provided in, for example, U.S. Pat. No. 8,471,100 (see, for example, columns 4 and 5), which is incorporated herein by reference in its entirety.

In one embodiment of the current invention, the binding agent that binds to SAB protein or RNA encoding SAB protein is labeled to facilitate the determination of the level of SAB protein or RNA encoding SAB protein in the sample. Non-limiting examples of such labels include fluorescent molecules, radioactive molecules, enzymes, chromogenic substrates, and fluorogenic substrates. Additional examples of labels and/or other techniques of visualizing the specific binding between the agent and the SAB protein or RNA encoding SAB protein in a sample are well known to a person of ordinary skill in the art and such embodiments are within the purview of the current invention.

In another embodiment of the current invention, the kit comprises a second agent that binds to the binding agent wherein the second agent is labeled to facilitate the determination of the level of SAB protein or RNA encoding SAB protein in the sample. Non-limiting examples of such labels include fluorescent molecules, radioactive molecules, enzymes, chromogenic substrates, and fluorogenic substrates.

In one embodiment of the invention, the kit further comprises a control sample. The control sample can be:
a) a sample obtained from an individual known to be free from the disease or known to have a low likelihood of developing the disease, or
b) a sample containing SAB protein or the RNA encoding SAB protein at a maximum level which is known to indicate the absence of the disease or a low likelihood of developing the disease.

Additional description about the control samples provided previously is also applicable to the kits of the current invention.

The kits of the current invention may further comprise other reagents useful for determining the level(s) of SAB protein or RNA encoding for SAB protein in a biological sample. The additional reagents can include, but are not limited to, reagents for preparation of biological samples, reagents for preparation of reaction mixtures, washing reagents, and reagents for visualization of the binding between the agent and the SAB protein or RNA encoding SAB protein. Additional components suitable for inclusion in the kits are well known to a person of ordinary skill in the art and such components are within the purview of the current invention.

Apoptosis-inducing chemotherapeutic agents for treatment against cancer can produce more severe side effects in aged subjects that in young subjects. This increased sensitivity is associated with increased levels of SAB in the mitochondria of the cells from the aged subjects compared to young subjects. Reducing SAB levels and/or inhibiting the activity of SAB protein in the mitochondria of the cells from the aged subjects can reduce the severity of the side effects induced by the chemotherapeutic agents in these subjects.

Accordingly, one embodiment of the current invention provides SAB-mediated signaling as a target to prevent non-specific chemotherapeutic toxicity. For example, small molecule inhibitors of SAB-mediated signaling can be administered in a subject to delay and/or prevent non-specific toxicity associated with chemotherapeutic agents.

In one embodiment, the current invention provides a method for protecting a subject from toxicity associated with an apoptosis-inducing chemotherapeutic agent, the method comprising administering to the subject an inhibitor of SAB-mediated signaling in an amount sufficient to delay and/or prevent non-specific toxicity associated with the apoptosis inducing chemotherapeutic agents. An example of the inhibitor of SAB-mediated signaling is a compound that reduces the expression and/or activity of SAB protein.

A further embodiment of the invention provides a method of assessing susceptibility of a cancer in a subject to a chemotherapeutic treatment and optionally, treating the subject with the chemotherapeutic treatment for the cancer, the method comprising the steps of:
a) determining the level of SAB protein or the RNA encoding SAB protein in a biological sample obtained from the subject;
b) determining the level of SAB protein or the RNA encoding SAB protein in a control sample;
c) identifying the subject as being susceptible to the chemotherapeutic treatment if the biological sample obtained from the subject has an increased level of SAB protein or the RNA encoding SAB protein relative to the level of SAB protein or the RNA encoding SAB protein in the control sample;
d) administering the chemotherapeutic treatment for the cancer to the subject identified as being susceptible to the chemotherapeutic treatment.

The cancer can be selected from, for example, leukemia, bladder cancer, bone cancer, brain tumor, central nervous system tumors, brain and spinal cord tumors, breast cancer, bronchial tumors, Burkitt lymphoma, gastrointestinal cancer, cervical cancer, colorectal cancer, esophageal cancer, head and neck cancer, liver cancer, Hodgkin lymphoma, islet cell tumors (endocrine pancreas), Kaposi sarcoma, kidney cancer, laryngeal cancer, lip and oral cavity cancer, lung cancer, non-small cell lung cancer, small cell lymphoma, AIDS-related lymphoma, Burkitt lymphoma, cutaneous T-cell lymphoma, non-Hodgkin lymphoma, ovarian cancer, testicular cancer, and vaginal cancer.

In a certain embodiment, the biological sample obtained from the subject is or comprises cancer cells.

The step of determining the level of SAB protein in the biological sample from the subject can be performed by, for example, immublotting, immunoprecipitation, immunofluorescence, immunostaining, immunoelectrophoresis, or enzyme-linked immunosorbent assay (ELISA). In a particular embodiment, the immunofluorescence technique is in-cell western blotting technique.

A further embodiment of the invention provides a method for identifying an agent for increasing the effectiveness of a cancer treatment by increasing mitochondrial priming, the method comprising the steps of:
a) screening potential compounds for their ability that increases SAB expression in a cell, b) optionally, screening the potential compounds for their ability to increase mitochondrial membrane depolarization, and c) identifying a compound capable of increasing SAB expression and/or increasing mitochondrial membrane depolarization as the agent for increasing the effectiveness of a cancer treatment.

The methods of screening according to the current invention can be performed on cancer cells, for example, ovarian cancer cells. Other cancer cells can also be used for screening potential compounds as therapeutic agents, adjuvants, chemosensitizers, etc. according to the methods of the current invention.

Materials and Methods:

Materials:

HeLa cells were obtained from American Type Tissue Culture (Manassas, Va.) and the wild type (WT) and JNK1$^{-/-}$/JNK2$^{-/-}$ murine embryonic fibroblasts (MEFs) were gifts. General laboratory media, reagents, and chemicals were acquired through Fisher Scientific (Waltham, Mass.). LY294002 (2-Morpholin-4-yl-8-phenylchromen-4-one) was purchased from Cell Signaling Technologies (Danvers, Mass.). Paclitaxel was supplied by LC Laboratories (Woburn, Mass.). Cisplatin was purchased from Sigma-Aldrich (St. Louis, Mo.). Antibodies were obtained from multiple vendors.

Cell Culture

HeLa cells, WT, and JNK1$^{-/-}$/JNK2$^{-/-}$ were cultured in Dulbucco's Modified Essential Media (DMEM) supplemented with 10% fetal bovine serum, 100 U/mL penicillin, 10 µg/mL streptomycin, and 5 µg/mL plasmocin. Cells were maintained at 37° C. under 5% $CO_2$ for no more than 25 passages after thawing.

LY294002 Treatment

LY294002 was solubilized in dimethylformamide (DMF). HeLa cells were exposed to the indicated doses of LY294002 over 24 h for acute studies. The 24-h IC$_{10}$ for LY294002 in HeLa cells to be ~2 µM. For sub-chronic exposure, cells were dosed with 2 µM LY294002 for seven days. The media was exchanged every 48 h to sustain the drug concentrations.

Calculation of Paclitaxel and Cisplatin IC$_{50}$s

The IC$_{50}$s for paclitaxel and cisplatin in HeLa cells were determined using the TO-PRO-3 near infrared dye (Invitrogen). Briefly, 10,000 cells were plated in a black-walled optically clear bottom 96-well plate. Cells were then exposed to increasing concentrations of paclitaxel (0-100 µM) or cisplatin (0-1 µM) for 24 h. The cells were fixed in 4% paraformaldehyde for 25 min at room temperature, and stained with TO-PRO-3 (1 µM) in PBST (150 mM NaCl, 8 mM $Na_2HPO_4$, 3 mM KCl, 2 mM $KH_2PO_4$, pH 7.4, 0.05% Tween 20). The cells were then washed five times in PBST while gently rocking for 5 min at room temperature. Samples were protected from light during incubations. Assays were visualized on the Li-Cor Odyssey CLx imager, and IC$_{50}$s were calculated using Graphpad® Prism.

Cell Lysis and Western Blotting

Following 72 h of transfection, cells were lysed and proteins were harvested. Protein concentration was determined using the by Pierce BCA Assay kit. Proteins were resolved by SDS-PAGE, and transferred onto PVDF membranes. Membranes were incubated with Li-Cor Biosciences Odyssey Blocking for at least 1 h at room temperature. The membranes were then incubated with primary antibodies specific for Sab, JNK, p44/42 MAPK (Erk1/2), p38, GAPDH, Actin, Calnexin, TOM20, or α-tubulin at 1:1000 dilutions in blocking buffer. Membranes were washed three times for 5 min in PBST. Membranes were incubated with secondary antibodies in blocking buffer at 1:20,000 for fluorescently conjugated secondary antibodies. Membranes were again washed three times for 5 min in PBST. Western blots were developed using the Odyssey CLx imager (Li-Cor Biosciences).

Mitochondrial Isolation

Mitochondria were isolated from HeLa cells. Mitochondrial samples with greater than 80% purity were used. A sample size of 50 µg mitochondrial protein was used for each protein analysis.

Site-Directed Mutagenesis

To generate a variant of Sab incapable of supporting signaling, site-directed mutagenesis was performed to alter the kinase interacting motifs 1 and 2 (KIM1/2) to prevent the binding of MAPKs, specifically JNK. Leucine 347 and 349 of the KIM1 motif and leucine 434 and 436 of KIM2 were mutated to alanine within Sab using a two reaction mutagenesis of the pLOC:Sab plasmid. First, KIM1 was mutated using sense (5'-GTGAGGCCTGGCAGCGCGGATGCGC-CCAGCCCTGTGTC-3', SEQ ID NO: 1) and antisense (5'-GACACAGGGCTGGGCGCATCCGCGCTGCCAG-GCCTCAC-3', SEQ ID NO: 2) oligonucleotides harboring the leucine to alanine mutations. The reaction was assembled using the Phusion site-directed mutagenesis kit (Thermo Scientific). The KIM1 mutations were confirmed by sequencing.

The KIM2 mutations were introduced using sense (5'-GAGAACCGGATGAAGCAGGCCTCCGCACAGTGCT-CAAAGGGAAG-3', SEQ ID NO: 3) and antisense (5'-GACACAGGGCTGGGCGCATCCGCGCTGCCAGGCC TCAC-3', SEQ ID NO: 4) oligonucleotides containing the appropriate mutagenic sequences. Following mutagenesis, single clones containing the double mutation of KIM1 and KIM2 were confirmed by sequencing. The resulting plasmid was named pLOC:Sab:KIM1/2 L-A. Similarly, silent mutations were introduced into Sab expression constructs to confer resistance to Sab shRNA #2 (TCRN0000139619-5'-CCTGTCAGAGTTTGGGATG-3', SEQ ID NO: 5). Sense (5'-TGTG TCCCTTTCGGAATTT-3', SEQ ID NO: 6) and anti-sense (5'-AACACTGGGAACATCATCCC-3', SEQ ID NO: 7) primers were used to introduce the desired mutations using the Phusion site directed mutagenesis kit. The mutated plasmid was named pLOC:Sab:shRNA$^r$.

Ectopic Expression and Silencing

Transient transfections with pLOC plasmids for expression and pLKO.1 plasmids for silencing (Open Biosystems) were used to modulate Sab levels. HeLa cells were plated at a density of 2×10$^5$ cells per 35-mm dish the day before transfections. Plasmids were mixed with FugeneHD (Promega) at a ratio of 3:1 according to the manufacturer's protocol. Protein levels were monitored by western blot analysis.

Western Blot Quantification

Western blot images were acquired using the LI-COR Odyssey CLx imager. Fluorescence signals were acquired for the bands of interest. Signals were adjusted to background and area using the ImageStudio software (LI-COR Biosciences). For analysis of protein signals, signal intensity for each band was divided by the signal of the corresponding loading control band in the same lane. For mitochondrial proteins (Sab), the intensity of the band of interest was divided by the fluorescent intensity of the COX-IV band. Cytosolic protein (Phospho-JNK) band intensities were divided by the fluorescent intensity of the α-tubulin band intensity. The quotient of each lane was then divided by the quotient for untreated cells. This allowed the expression to be normalized to a value of 1. The mid-tones (K-value) for each image were unchanged and maintained at a value of 0 for each analysis. The data represented in each figure represents a minimum of three biological replicates.

Biological Replicates and Statistics

A minimum of eight biological replicates were measured for cell-based studies. Biochemical assays, fluorometric detection of superoxide, and other cellular measures were performed with a minimum of six experimental replicates. To determine statistical significance, Student's paired t test was employed for significance between treatments. Statistical significance is indicated by an asterisk (*) in figures in which the p-value is less than 0.05, and p-values less than 0.01 are indicated by two asterisks (**). Non-significant results are unlabeled or indicated by "n.s." Data are displayed as means with error bars representing plus and minus one standard deviation from the mean.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and that various modifications or changes in light thereof will be suggested to persons skilled in the art and are to be included within the spirit and purview of this application.

Example 1—In-Cell Western Blot Analysis

Cells or tissue samples are placed in a fluorescent compatible plate (for example, a 96-well plate) and the sample can be fixed to the plate. The sample is then permeabilized using detergent to disrupt the plasma membrane. Primary antibodies to detect SAB (Abnova, Inc.) are then incubated with the samples. Following a brief wash, the cells are incubated with a fluorescently labeled secondary antibody used to recognize the primary antibody. The samples are washed again. The plate is then scanned on a Li-Cor Bioscience Odyssey CLx near-infrared scanner to measure the fluorescent signal from the sample. A high fluorescent signaling indicates a higher level of SAB protein, while a low fluorescence signal indicates a lower level of SAB protein.

This assay can be used to detect SAB protein concentrations in a variety of cells and tissues. The assay can be useful for adherent cells, non-adherent cell, and primary cells. The assay can be modified to detect the level of SAB protein in biological samples from blood, muscle, adipose, brain, nerve, cardiac, liver, kidney, testicle, ovary, and other low fluorescent tissues.

Example 2—SAB Levels in Various Disease Conditions

Parkinson's disease-like state was induced in animals by localizing treatment to the ventral midbrains of rats using 6-hydroxydopamine. Blood was obtained from 6-hydroxydopamine treated rats and the control rats. Levels of SAB protein or RNA encoding SAB proteins in platelets and other blood cells were higher in 6-hydroxydopamine treated rats compared to control rats.

Similarly, blood samples can be obtained from humans suffering from Parkinson's disease and humans free from Parkinson's disease. Levels of SAB protein or RNA encoding SAB proteins in platelets and other blood cells will be higher in the humans suffering from Parkinson's disease compared to the humans free from Parkinson's disease.

Tissues samples from ventral midbrain and muscles were obtained from young rats and aged rats. SAB protein levels were determined in the two sets of samples. SAB levels were higher in the ventral midbrains and muscles of aged rats compared to SAB levels in the young rats.

Over-expression of SAB protein in muscle cells accelerated muscular atrophy in the presence of wasting stimuli.

Further, disrupting SAB-mediated signaling interferes with adipogenesis. During adipogenesis, SAB levels increased prior to loss of mitochondrial membrane potential and mitophagy during differentiation.

Figure 10:
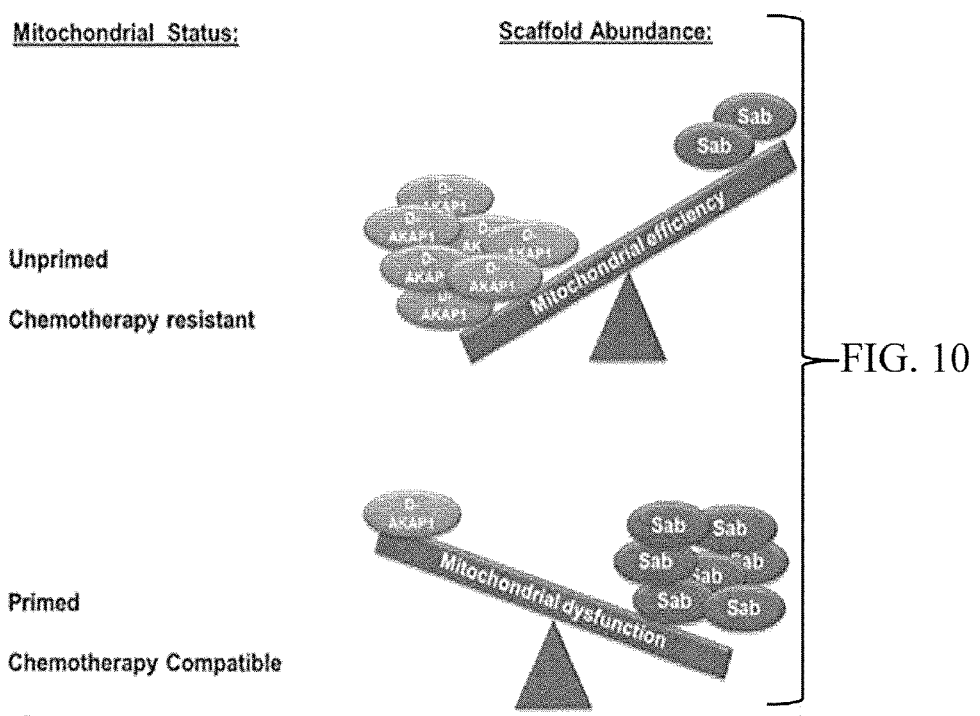
FIG. 10 shows a schematic representation of the correlation between SAB expression, mitochondrial priming, and susceptibility of a cell to apoptosis induced by a chemotherapeutic agent.

Example 3—Correlation Between SAB Expression, Mitochondrial Priming, and Susceptibility of a Cancer to Apoptosis Inducing Chemotherapeutic Agents Mitochondrial priming influences cancer cell responses to chemotherapy. Mitochondrial priming is the process potentiating mitochondrial physiology towards a pro-apoptotic response. In cancer cells, mitochondrial priming has been used as means to sensitize cells to chemotherapy and radiotherapy approaches. Mitochondrial priming drives cancer cells toward apoptosis by exploiting their unique biology and permits physicians to administer lower doses of toxic chemotherapies. The amount of mitochondrial priming can be used as a predictive index of chemotherapeutic success. Elevated levels of pro-apoptotic Bcl-2 family members are seen on primed mitochondria. Therefore, detection of primed mitochondria in tumors can be used as a biomarker for chemotherapeutic success (FIG. 10).

HeLa cell mitochondria were primed using a sub-chronic (2 μM dose) of LY294002 for seven days. The concentration of SAB was monitored using quantitative western blot analysis on protein lysates taken on days 0, 3, and 7 of LY294002 treatment. As the treatment progressed, a pronounced increase in SAB expression was observed on days 3 and 7 of priming (FIG. 1). These data suggest that SAB is elevated on primed mitochondria.

SAB levels also increased in response to other chronic cytotoxic processes, namely aging, sub-chronic administration of Parkinson's disease mimetics, and treatment with carbonylcyanide m-chlorophenylhydrazone (CCCP).

Figure 2:
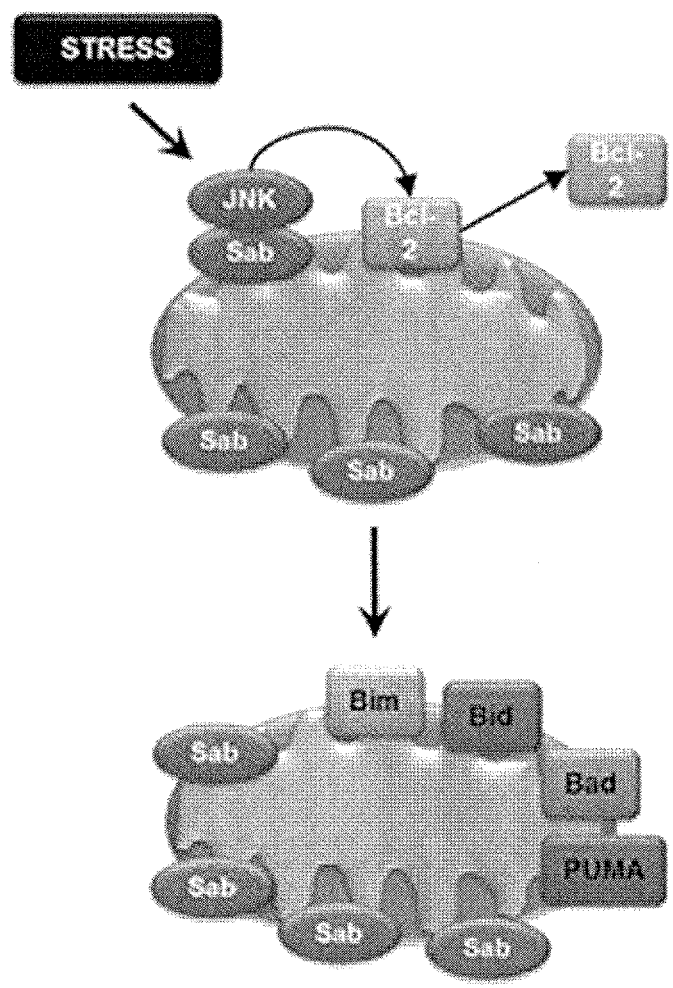
FIG. 2 shows schematic representation of the temporal relationship between SAB-mediated signaling and known mitochondrial priming events.

Based on the relationship between mitochondrial c-Jun N-terminal Kinase (JNK) signaling and emigration of Bcl-2 from the mitochondria, SAB increases may precede migration of pro-apoptotic Bcl-2 family members migration to mitochondria (FIG. 2). Therefore, detecting SAB levels in tumor specimens can be used to identify patients that can be treated with apoptosis-inducing chemotherapies and/or radiation therapies.

Primed mitochondria do not necessitate the presence of pro-apoptotic Bcl-2 family proteins. The current methods used to detect primed mitochondria evaluate the presence of pro-apoptotic Bcl-2 family members and monitor the loss of mitochondrial membrane potential. These are late stage markers of mitochondrial dysfunction and apoptosis. Using these markers may limit the number of cancers considered susceptible to apoptosis inducing chemotherapies and/or radiation therapies.

By employing SAB as a diagnostic marker to identify early primed mitochondria, the number of cancers deemed susceptible to apoptosis inducing chemotherapies and/or radiation therapies can be increased.

Over-Expression of SAB in Cancer Cells Increases Chemotherapeutic Susceptibility In Vitro Artificially increasing SAB expression in cells is sufficient to increase chemotherapeutic sensitivity. SAB is over-expressed using lentivirus transduction and chemotherapeutic toxicity for cancer cell lines and normal fibroblasts is determined.

HeLa (cervical carcinoma), HepG2 (hepatocellular carcinoma), SH-SY5Y (neuroblastoma), MCF-7 (breast cancer), SKOV3 (ovarian cancer), and DU145 (prostate cancer) cells are used for this purpose. These cell lines represent a broad selection of cancers. IMR-90 cells, normal human lung fibroblasts, are used as a non-cancer control to observe the impact of SAB over-expression on normal cell mitochondrial priming.

SAB is overexpressed in cancer cells after transfection with lentivirus transduction. Viral particles capable of expressing SAB protein is obtained from Open Biosystems, Inc. (ThermoFisher). A virus that over-expresses humanized green fluorescent protein is used as a control. Over-expression of SAB is confirmed by quantitative western blot analysis and proper localization is determined by immune-fluorescent microscopy.

Evaluation of Chemotherapeutic Priming in Cancer Cells

Mitochondria are isolated from the cells. Following assessment of mitochondrial purity, quantitative western blot analysis is performed for Bcl-2 family members that may indicate the extent of priming. Mitochondria are examined for levels of anti-apoptotic (Bcl-2 and Bcl-XL), pro-apoptotic sensitizing (Bim, Bid, Bad, and Puma) and apoptotic activating (Bax and Bak) members of the Bcl-2 family of proteins. Flow cytometry based methods are also used to detect Bcl-2 family members.

High levels of Bcl-2 and Bcl-XL indicate the cells are not primed, while elevated levels of Bax and Bak indicate a terminal commitment to apoptosis. Primed mitochondria have an abundance of sensitizing Bcl-2 family members. SAB over-expression creates a mitochondrial state with a distribution of anti-apoptotic and sensitizing members of the Bcl-2 family with little to no Bax or Bak present on mitochondria.

One of the final events in mitochondrial dysfunction and apoptosis is the loss of mitochondrial membrane potential. JC-1 dye is used to identify loss of mitochondrial membrane potential. This detection method is chosen because the transition from red fluorescent aggregates to green fluorescent monomers can be detected quantitatively by fluorometer and validated qualitatively by microscopy. Alternatively, Tetramethylrhodamine (TMRM) is also as an option. Additionally, fluorescently labeled glucose uptake is used to monitor loss of mitochondrial membrane potential on isolated mitochondria. Overexpression of SAB induces some of these late mitochondrial priming events.

Determining Chemotherapeutic Susceptibility in Fibroblasts and Cancer Cells Over-Expressing SAB A panel of drugs targeting different aspects of cancer cell biology are chosen. 2-deoxy-D-glucose (2-DOG) is a potent inhibitor of hexokinase, the first enzyme in glycolysis. Most cancer cells up-regulate glycolysis to have sufficient carbon for biosynthesis and proliferation in addition to energy production. SAB-mediated signaling improves metabolic transformation of cancer cells leading to a change in sensitivity when SAB is over-expressed in cancer and IMR-90 cells. Since phosphoinositol-3 kinase (PI3K) signaling has been implicated in the metabolic shift of cancer cells, LY294002 can have a similar effect on cancer cell and IMR-90 cells.

Apoptosis is induced by Cisplatin, an activator of caspase 3, 6-mercaptopurine, an inhibitor of RNA and DNA synthesis, or by docetaxel.

To accurately determine the lethal dose ($LD_{50}$) of the drugs in the presence or absence of elevated SAB levels, a 96-well plate based assay is used thereby monitoring large dose curve to help narrow down the $LD_{50}$. For example, LIVE/DEAD Viability/Cytotoxicity Assay Kit (Invitrogen) is used to determine the $LD_{50}$. This kit uses fluorescent dyes calcein and ethidium. Live cells stained with calcein fluoresce green, while dying cells fluoresce red. The results of this kit can be validated with an MTT assay; however, this approach is heavily reliant on mitochondria and can be misleading in cells that have extensive mitochondria priming, as the development of dysfunctional but non-toxic mitochondrial populations falsely lowers the assay signal. Over-expression of SAB lowers the $LD_{50}$ of these drugs in cancer and IMR-90 cells that over-express SAB.

Profiling of Cancer Cell Lines Reveals Lines with Elevated SAB Expression are Susceptible to Chemotherapy Commercially-available validated tumor cell panels are surveyed for SAB abundance by quantitative western. These findings are correlated with known chemotherapeutic sensitivities of cell lines.

Selection of tumor cell panels: Cancer cell panels available from American Type Culture Collection (ATCC), are chosen. ATCC have collected several tumor panels based on tissue types, for example, bladder, bone, brain, breast, colon, gynecologic, head/neck, liver, lung, pancreas, skin, and stomach.

In-Cell Western Analysis to Detect SAB-Expression in a High-Throughput Manner

An in-cell western allows detection of protein levels in cells cultured in a 96-well black walled plate. For this technique, the cells are fixed with paraformaldehyde following seeding and growth to 80% confluency. The cells are then permeabilized by a Tris buffer containing Triton X-100. The cells are blocked using blocking buffer (5% bovine serum albumin in Tris-Buffered Saline). The cells are then incubated with primary antibodies for SAB and a loading control (actin) to assure equal cell abundance from well-to-well. Then conjugated secondary antibodies with near infrared fluorophores (emission at 700 and 800 nm) are incubated with the cells. The secondary antibodies are specific for the hosts of the primary antibodies—SAB (mouse) and Actin (rabbit); thus, SAB signals are emitted at 700 nm and Actin emitted at 800 nm. Using the LiCor Odyssey CLx near infrared imager, the relative amounts of protein in each well are quantified. Cells with primed mitochondria have increased levels of SAB and are more sensitive to apoptosis inducing chemotherapies and/or radiation therapies.

An example of in-cell western technology for the detection of SAB is shown in (FIG. 3). The assay has a Z' of 0.72 for cells treated with increasing LY294002 concentration as a means to elevate SAB expression (FIGS. 3A-3C). In a model of cytotoxicity, SH-SY5Y cells treated with increasing sub-chronic doses of the neurotoxin, 6-hydroxydopamine (6-OHDA) were seeded in a 96-well plate and monitored for SAB expression. Treatment with 6-OHDA elevates SAB expression as indicated by the in-cell western approach (FIG. 4).

Example 4—Correlation Between Age-Dependent Chemotherapeutic Toxicity and SAB Mediated Signaling A major problem with aging cancer patients is the incompatibility of the aggressive nature of chemotherapy with the degenerating physiology of elderly individuals. This is a problem that will increase in spectrum (gender, ethnicity, genetics, cancer type, etc.) and number as our population ages. It is imperative to understand the physiological changes contributing to age-dependent chemotherapeutic toxicity, so physicians may more accurately prescribe treatment regimens for the patients.

It is apparent that each individual ages differently with respect to physical appearance and physical and cognitive activity; however, molecular examination of aging reveals a single commonality among different individuals.

Mitochondrial dysfunction (although it occurs at different rates in individuals during aging due to a variety of factors) is a hallmark of aging. As individuals age, they accumulate mutations in mitochondrial DNA (mtDNA) as well as damaged mitochondria from normal function and a lifetime of stress exposures. The culmination of these events polarizes mitochondria toward apoptosis.

The polarization of mitochondria towards apoptosis is often a strategy employed in healthy individuals undergoing chemo- or radiotherapy. Sensitizers are used to increase the effectiveness of chemotherapy and radiotherapy in cancer patients. One family of sensitizers is based on the chemical LY294002, which is a PI3K inhibitor. Treatment with these inhibitors, including LY303511, alters signal transduction in cancer cells to promote cell death. Once sensitized, a patient can be subjected to chemotherapies or radiation to kill the cancer cells.

This sensitization process alters mitochondrial physiology in order to promote a pro-apoptotic environment in the cell. The use of sensitizers may complicate the administration of the final therapy in aged individuals because the pro-apoptotic potential of normal cells in these individuals is not known. Thus, providing individuals with toxic broad spectrum chemotherapeutics could have damaging side-effects, including death.

SAB-Mediated Signaling and Cell Death

Mitochondrial scaffold protein, SAB, is required for induction of mitochondrial dysfunction and cell death. While examining SAB signaling, a small, cell permeable peptide designed to prevent protein-protein interactions at the kinase interacting motif 1 (KIM1) motif of SAB was developed called Tat-SAB$_{KIM1}$ peptide. Use of this peptide prevents anisomycin-induced mitochondrial dysfunction and cell death in HeLa cells. This observation suggests that SAB-mediated signaling is a crucial component in pro-apoptotic responses.

SAB-Mediated Signaling as a Target for Human Disease

Using models of Parkinson's disease (PD) and myocardial infarction (MI), the therapeutic potential for Tat-SAB$_{KIM1}$ in the rat 6-hydroxydopamine (6-OHDA) model of PD and the rat ischemia/reperfusion (I/R) model of MI was examined. In the 6-OHDA model of PD, administration of the Tat-SAB$_{KIM1}$ peptide directly into the substantia nigra prevented 6-OHDA-induced neurotoxicity and motor deficit. Similarly, direct injection of the Tat-SAB$_{KIM1}$ peptide into the left ventricle of rats prevented I/R-associated oxidative stress and cardiotoxicity. Further, two other research groups have independently demonstrated that disrupting SAB mediated signaling protects against neonatal ischemic injury and acetaminophen-induced hepatotoxicity.

Chemotherapeutic Sensitizer, LY294002, Increases SAB Expression in HeLa Cells

To determine if SAB-mediated signaling is involved in polarizing cells toward apoptosis, SAB expression was examined in the presence of the chemotherapeutic sensitizer, LY294002, an inhibitor of PI3K. LY294002 has been used prior to chemotherapies to lower the dose required. This strategy is used to reduce patient exposure to toxic chemotherapeutic agents. Since LY294002 is shown to potentiate apoptotic responses in cancer cells, SAB expression was examined in HeLa cells treated with 2 µM LY294002 for seven days. A comparison of untreated cells and cells treated with LY294002 revealed that HeLa cells treated with LY294002 had a significant increase in SAB expression compared to untreated controls. This indicates SAB-mediated signaling is involved in polarizing cells for apoptosis.

SAB Concentration Increases with Age in Mice

Figure 5:
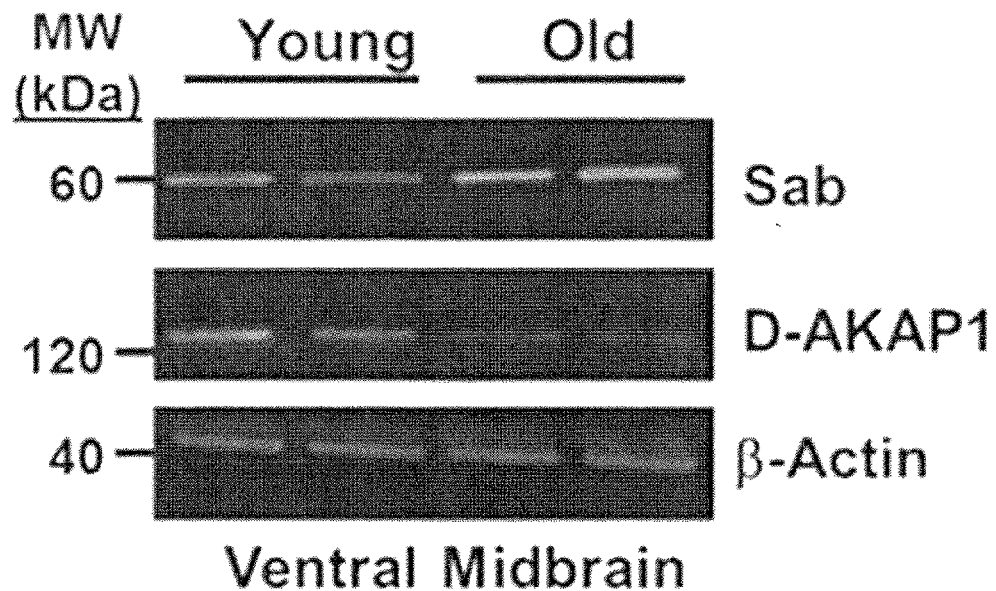
FIG. 5 shows SAB expression increased in aged mice.

To determine if the increase in SAB expression seen with LY294002 was an age-related phenomenon, SAB expression in the ventral midbrain of young (5 months) and aged (15 months) mice was examined (FIG. 5). The ventral midbrain was chosen for examination because the ventral midbrain is a site of degeneration in aged mammals; consequently, cells in this region should become polarized for apoptosis in this region. Examination of SAB expression by western blot of mitochondrial preparations from the ventral midbrains shows a clear increase in SAB expression with age. This result suggests that SAB levels increase and contribute to non-specific chemotherapeutic toxicity.

The current invention provides that elevation in SAB concentration with age polarizes cells toward cell death. This effectively increases the cells' sensitivity to apoptosis inducing chemotherapeutic agents. This increased sensitivity may contribute to non-specific chemotherapeutic toxicity in aged patients. Therefore, the current invention provides that targeting SAB-mediated signaling in low doses may be an effective mechanism to prevent non-specific chemotherapeutic toxicity in older patients.

Off-target chemotherapeutic toxicity is of significant concern in older cancer patients when selecting a chemotherapeutic regimen. The current invention provides that mitochondria become predisposed to initiating apoptosis during aging in response to a lifetime of stress exposure (disease, inflammation, injuries, etc.). The culmination of these exposures leads to elevated levels of the mitochondrial protein scaffold SAB, which potentiates mitochondrial signaling toward induction of cell death. The current invention further provides that since chemotherapeutic toxicity increases with age due to increasing mitochondrial dysfunction, targeting SAB-mediated signaling provides a therapeutic option to decrease age-dependent chemotherapeutic toxicity.

SAB-Mediated Signaling is a Critical Element of Age-Dependent Chemotherapeutic Toxicity and Represents a Therapeutic Target to Protect Against Chemotherapeutic Toxicity The current invention provides SAB-mediated signaling as a target to prevent non-specific chemotherapeutic toxicity. For example, small molecule inhibitors of SAB-mediated signaling can be administered at low doses in patients to delay and/or prevent non-specific toxicity associated with chemotherapeutic agents.

Selection of "Normal" Cell Line

To determine the impact of SAB-mediated signaling on sensitivity to chemotherapeutics in normal cells a non-immortalized cell is used. An example of such a cell line is IMR-90 cell line which is a not mal human lung fibroblast cell line commonly used to display basal changes in cell biology.

Also, SAB is exogenously over-expressed to avoid confounding of the results due to LY294002 induced artificial over-expression of SAB protein.

Lentiviral-Mediated Over-Expression of SAB in IMR-90 Cells

Since aging and treatment with a sensitizer both elevate SAB levels, whether SAB expression in IMR-90 cells is sufficient to potentiate cells toward apoptosis and reduce sensitivity to distinct chemotherapeutic agents is examined. SAB is over-expressed using lentiviral particles purchased from Open Biosystems, Inc. (ThermoFisher) capable of over-expressing SAB under control of a human cytomegalovirus promoter. Infection is monitored by fluorescence, as the lentiviruses encode red fluorescent protein. Successfully infected cells fluoresce red. SAB over-expression is monitored by quantitative western blotting using the LiCor Odyssey Clx near-infrared imager.

Adenoviruses can also be used to over-express SAB. Consequently, cells' resistance to chemotherapeutic agents rather than polarization toward apoptosis is monitored.

As a control for over-expressing a protein in IMR-90 cells, a second virus is ordered that over-expresses humanized green fluorescent protein (hGFP).

Selection of Chemotherapeutic Agents

A panel of drugs targeting different aspects of cancer cell biology is chosen. 2-deoxy-D-glucose (2-DOG) is a potent inhibitor of hexokinase, the first enzyme in glycolysis. Most cancer cells up-regulate glycolysis to have sufficient carbon for biosynthesis and proliferation in addition to energy production. SAB-mediated signaling improves metabolic transformation of cancer cells leading to a change in sensitivity when SAB is over-expressed in cancer and IMR-90 cells. Since PI3K signaling has been implicated in the metabolic shift of cancer cells, LY294002 can have a similar effect on cancer cell and IMR-90 cells.

Measuring Mitochondrial Dysfunction by Monitoring Respiration, Superoxide Generation, and Mitochondrial Membrane Potential SAB-mediated signaling initiates mitochondrial dysfunction. Mitochondrial dysfunction is examined by monitoring mitochondrial respiration, superoxide production, and mitochondrial membrane potential for each of the drugs mentioned above in IMR-90 cells and IMR-90 cells over-expressing SAB or hGFP.

Measuring Mitochondrial Dysfunction Through Respiration

When mitochondria become dysfunctional, they lose the ability to properly perform metabolism. This is manifested by a decrease in oxygen consumption rate (OCR). OCR is measured using a Seahorse Bioscience XF-96 extracellular flux analyzer. This instrument can detect changes in oxygen levels in the extracellular media in real-time without destroying cells. Using this device, changes in basal OCR, uncoupled OCR, and reserve respiratory capacity are examined. This is achieved by treating cells with uncouplers, such as carbonyl cyanide 4-(trifluoromethoxy)phenylhydrazone (FCCP).

Superoxide Generation as a Measure of Mitochondrial Dysfunction

When mitochondrial metabolism or membrane potential is perturbed, mitochondrial respiratory complexes I and III undergo incomplete oxidation. The release of this electron into the matrix of mitochondria or into the extra-mitochondrial environment produces a superoxide ion. This mitochondrial superoxide can be detected selectively by a fluorescent dye, MitoSOX Red (Invitrogen). Quantitative fluorescence measurements are used for cells stained with MitoSOX Red to determine the relative amount of superoxide in the cells and treatments mentioned above. Alternatively, superoxide production is also monitored by Amplex Red assays on mitochondrial preparations isolated from cells.

Measuring Mitochondrial Membrane Potential with JC-1

One of the final events in mitochondrial dysfunction and apoptosis is the loss of mitochondrial membrane potential. JC-1 is used to examine mitochondrial membrane potential. The transition from red fluorescent aggregates to green fluorescent monomers can be detected quantitatively by fluorometer and validated qualitatively by microscopy. Alternatively, Tetramethylrhodamine (TMRM) can be used. Additionally, fluorescently labeled glucose uptake can also be used to monitor loss of mitochondrial membrane potential on isolated mitochondria. Over-expression of SAB induces mitochondrial dysfunction in IMR-90 cells.

Determining the $LD_{50}$ of Chemotherapeutic Compounds

To accurately determine the lethal dose ($LD_{50}$) of the drugs in the presence or absence of elevated SAB levels, a 96-well plate based assay is used thereby monitoring large dose curve to help narrow down the $LD_{50}$. For example, LIVE/DEAD Viability/Cytotoxicity Assay Kit (Invitrogen) is used to determine the $LD_{50}$. This kit uses fluorescent dyes calcein and ethidium. Live cells stained with calcein fluoresce green, while dying cells fluoresce red. The results of this kit can be validated with an MTT assay; however, this approach is heavily reliant on mitochondria and can be misleading in cells that have extensive mitochondria priming, as the development of dysfunctional but non-toxic mitochondrial populations falsely lowers the assay signal. Over-expression of SAB lowers the $LD_{50}$ of these drugs IMR-90 cells that over-express SAB.

Inhibition of SAB-Associated Signaling in Aged Mice

Manipulation of gene expression within liver in vivo is performed using recombinant adeno-associated viral (rAAV) transduction. rAAV is used because of its safety features and its ability to induce over-expression and gene silencing in vivo. Vector Biolabs is used to produce ready-to-inject rAAV particles to silence SAB expression using a small hairpin RNA (shRNA), viruses capable of silencing SAB expression, and control viruses (nonsense shRNA). The viruses express red fluorescent protein (RFP) in order to determine levels of infection post-mortem.

Delivery of rAAV Particles to Liver

Adenovirus particles are delivered to the liver by tail-vein injection with known techniques. Viral particles injected in this manner accumulate in the liver. Proper local analgesics are administered prior to injection of the particles. Particle numbers are optimized between a range of $1 \times 10^8$ particles and $1 \times 10^{12}$ particles per milliliter delivery volume.

Quantitation of Scaffold Concentration Change

The change in scaffold abundance is monitored using post-mortem quantitative western blot analysis for SAB on liver samples. Successful silencing is shown by decreased SAB levels in the livers of animals infected with viruses carrying the SAB shRNA-encoding DNA. Control viruses do not impact SAB expression in the liver.

Determining 6-Mecaptopurine-Induced Hepatotoxicity in Aged Mice

It is well established that doses of 6-mercaptopurine greater than 2 mg/kg can induce hepatotoxicity in patients. Pro-apoptotic potentiated mitochondria exhibit age-associated increase in the liver which enhances the toxicity of the drug. Therefore, administration of 2 mg/kg induces hepatotoxicity in old mice, but not young mice. Further, silencing SAB in older mice should reduce levels of hepatotoxicity attributed to 6-mercaptopurine administration. Once SAB is silenced (time to be determined), 6-mercaptopurine (2 mg/kg) is administered for up to 7-days (dependent upon time need to achieve hepatotoxicity in aged controls). Following treatment, animals are euthanized. Livers are dissected and histology is performed to determine hepatotoxicity. Also, other samples of the liver are used for mitochondrial isolation for observation of metabolism and mitochondrial dysfunction as described above.

Example 5—a Parkinson's Disease Diagnostic and Prognostic Assay Using the Novel Biomarker, SAB Parkinson's disease (PD) is the most common neurodegenerative disease in western societies. The manifestations associated with PD (loss of motor control, death, etc.) are a result of the loss of dopaminergic neurons in the substantia nigra of patients. While greater than 85% of the PD cases occur spontaneously, the only diagnostic assay available is a genetic test to identify mutations associated with familial PD. Recently, we have identified a protein on the mitochondria of human neuronal cells and in the ventral mid-brains of rats that increases in response to PD-mimicking stressors; this protein, called SAB, serves as a scaffold for cytotoxic signaling kinases, namely the JNK. Additionally, SAB serves as a nucleating site for signaling events that promote mitochondrial dysfunction, a hallmark of PD. Given the intimate relationship between PD, mitochondrial dysfunction and JNK, the current invention provides SAB as a useful biomarker in determining a patient's susceptibility to mitochondrial disease, namely PD.

In PD, mitochondrial dysfunction has not only been detected in the substantia nigra of patients, but it has also been detected systemically in platelets found in the blood of patients. Based on this, the current invention provides that SAB abundance in platelets from patient blood samples provides a high-throughput blood test to predict susceptibility and prognosis for PD.

Figure 6:
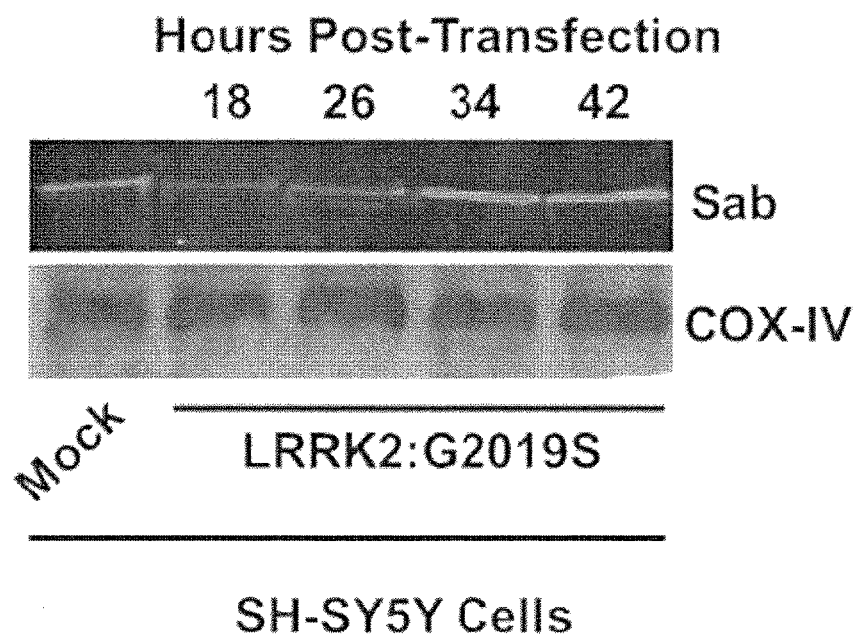
FIG. 6 shows Western blot of SH-SY5Y cells reveals that SAB levels increase at a time course comparable to PD-related mutant, LRRK2:G2019S. COX-IV was used as a loading control.
Figure 9:
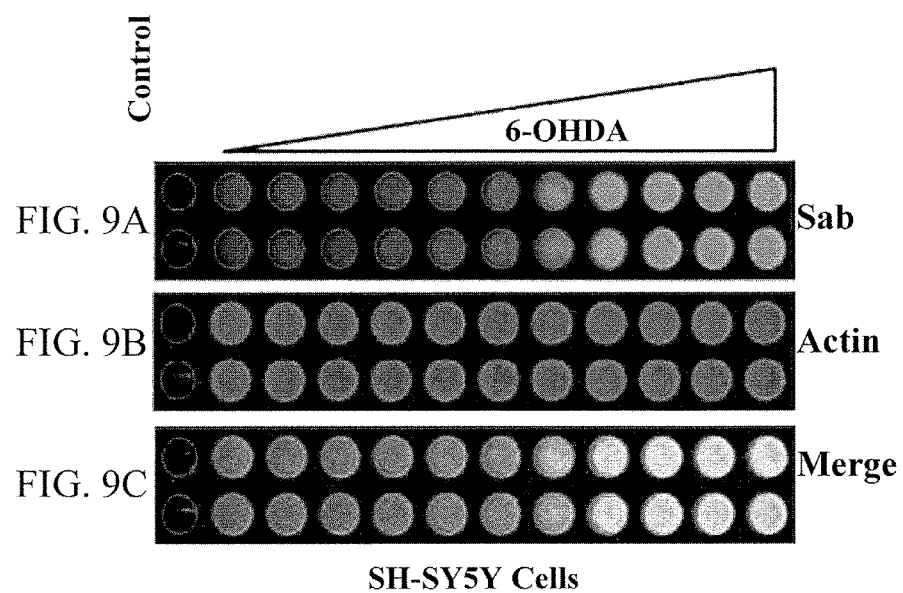
FIGS. 9A-9C show a full in-cell Western analysis with controls. The cells were treated with increasing amounts of 6-OHDA (0-100.00 nM). Cells were then analyzed for the amount of SAB after 24 hours, SAB levels increased in a dose-dependent manner with 6-OHDA (9A). Actin was used as a loading control (9B). The merger of the simultaneous in-cell westerns indicates the increase in SAB as demonstrated by the increasing amount of yellow (9C).

Changes in SAB levels both in cellular and animal models of PD were examined. Using human SH-SY5Y (neuroblastoma) cells expressing the PD-related mutant, LRRK2: G2019S, which represents a mutation that increases the kinase activity of the leucine-rich repeat kinase 2 (LRRK2), it was found that during the course of 42 hours SAB levels increased (FIG. 6). SH-SY5Y cells experienced 50% cell death at 48 hours of LRRK2:G2019S treatment indicating that SAB facilitates neurotoxic signaling in these cells. A similar effect was seen with the neurotoxin 6-hydroxydopamine (6-OHDA) in SH-SY5Y cells (FIGS. 9A-9C). 6-OHDA is a chemical that induces a PD-like state in cells and animals. Stereotactic injection of 6-OHDA into the substantia nigra of rats results in PD-like disease including loss of motor control.

Figure 7:
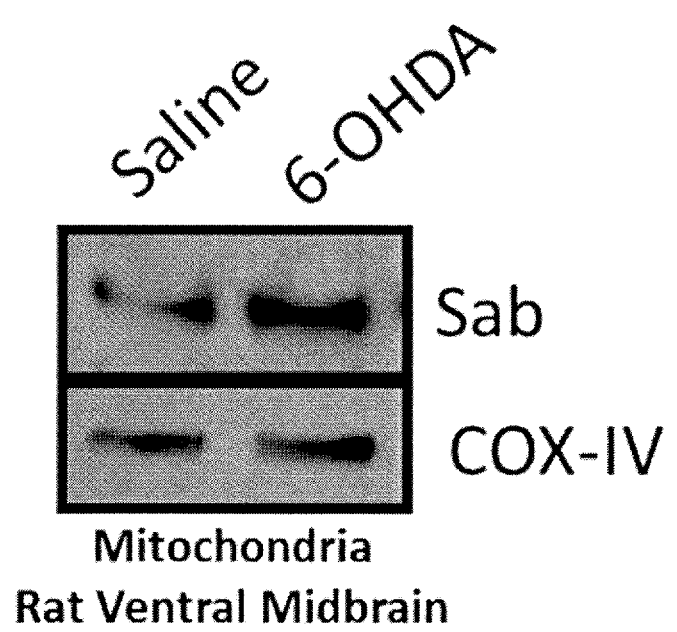
FIG. 7 shows a Western blot of the ventral midbrains indicating that SAB concentration is elevated in rats stereotactically injected with 6-OHDA. Samples were acquired six days post-injection. COX-IV was the loading control.
Figure 8:
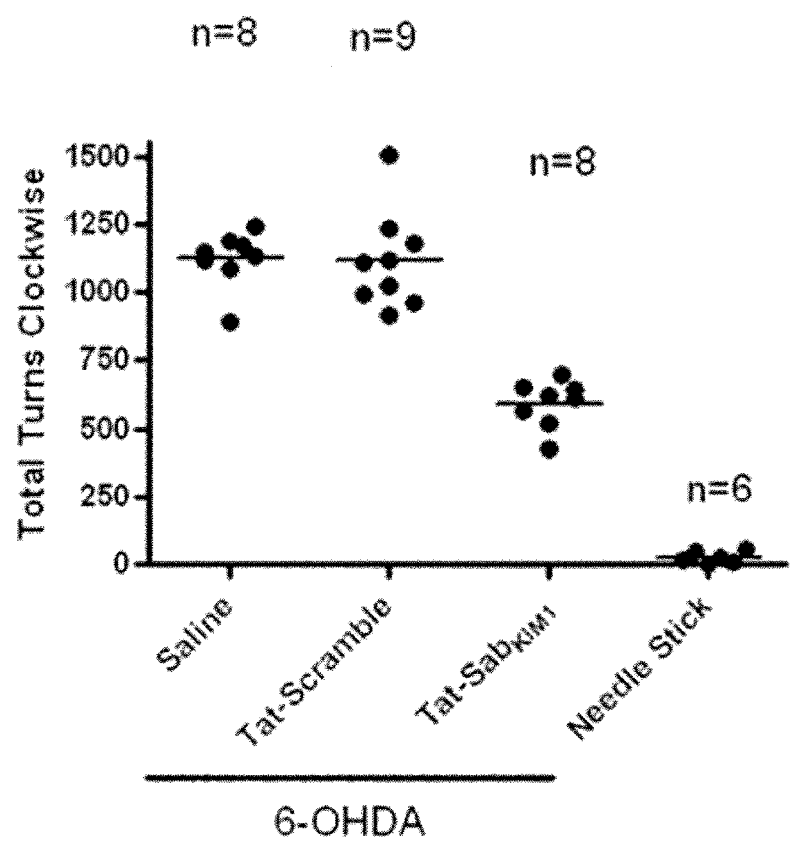
FIG. 8 shows motor deficit in rats was determined by amphetamine-induced turning. 6-OHDA induced injury to one hemisphere of the substantia nigra results in unilateral rotation. Clockwise turns were measured. Inhibition of SAB signaling decreased 6-OHDA induced motor deficit.

Examination of the ventral midbrain of rats injected with saline or 6-OHDA revealed that SAB levels increase after injection of 6-OHDA, but not after saline injection (FIG. 7). Further, disruption of SAB-mediated signaling using a small peptide to block kinase binding to SAB prevented 6-OHDA-induced motor deficiencies in rats (FIG. 8). These data suggest that signaling associated with SAB is necessary for PD-related pathophysiology.

This test serves as the first blood-based screening tool for PD. It allows not only patients with genetic mutations to know their susceptibility to PD, but also allows individuals with no genetic predisposition for PD to know their susceptibility to PD. Moreover, this assay serves as an indicator of PD progression, which helps not only the patient but family and friends to prepare for how quickly the disease will progress. This assay helps save lives and assist physicians in choosing proper treatment options.

Example 6—SH3BP5 Levels Indicate Ovarian Cancer Susceptibility to Conventional Therapies Ovarian cancer is the most lethal of all gynecologic malignancies. Although initial response rates for platinum-based chemotherapeutic regimens are high, most ovarian cancers recur. An embodiment of the current invention provides the impact of SH3BP5 expression on ovarian cancer mitochondria and its correlation to predicting sensitivity to chemotherapy. One embodiment of the current invention provides that SH3BP5 is a marker of mitochondrial priming for cell death, and the extent of mitochondrial priming in ovarian cancer indicates sensitivity to conventional chemotherapies. A high-throughput assay to detect the levels of SH3BP5 in ovarian cancer cells and its correlation to mitochondrial priming and chemotherapeutic sensitivity in ovarian cancer is provided. Further, therapeutic agents that elevate SH3BP5 expression, improve initial chemotherapeutic outcomes and reduce ovarian cancer recurrence are also provided.

Current chemotherapeutic methods for treating ovarian cancer include targeting angiogenesis, folate transporters, and dysregulated signaling pathways. However, few ovarian cancer therapies target mitochondria, the organelle responsible for regulating cell death responses.

Mitochondrial priming indicates cellular sensitivity to chemotherapy. Mitochondrial priming refers to a state prior to programmed cell death where mitochondria begin to accumulate BH3-only members of the Bcl-2 protein family causing a loss of mitochondrial membrane potential. This mitochondrial perturbation is common in non-adherent cancers such as leukemia, and it may be a predictive index for therapeutic susceptibility. However, current studies have only been performed on non-adherent cancers, and it is unclear if mitochondrial priming is applicable as a prognostic in solid tumors.

SH3BP5-mediated signaling enhances mitochondrial dysfunction and cell death. Mitochondrial signaling associated with the JNK has been implicated in apoptosis induced by chemotherapeutic compounds. JNK is localized to mitochondria via interaction with SH3BP5. Once on the mitochondrial surface, JNK signaling increases the production of reactive oxygen species, phosphorylates Bcl-2 on serine 70 (causes emigration from mitochondrial membranes), causes loss of mitochondrial membrane potential and induces cell death. SH3BP5 can also interact with p38 to promote apoptotic responses and cytosolic variants of SH3BP5 have been shown to inhibit Bruton's tyrosine kinase (BTK) and prevent B-cell proliferation and oxidative responses. The physiological consequence of mitochondrial JNK signaling is reminiscent of mitochondrial priming. HeLa cells treated for seven days with a chemosensitizer, LY294002, exhibit increased SH3BP5 expression (FIG. 1) indicating that mitochondrial scaffolds plays a role in mitochondrial priming.

Given the potential relationship between mitochondrial priming and SH3BP5-mediated signaling, the current invention provides the effect of SH3BP5 over-expression on ovarian cancer mitochondria.

Figure 11A:
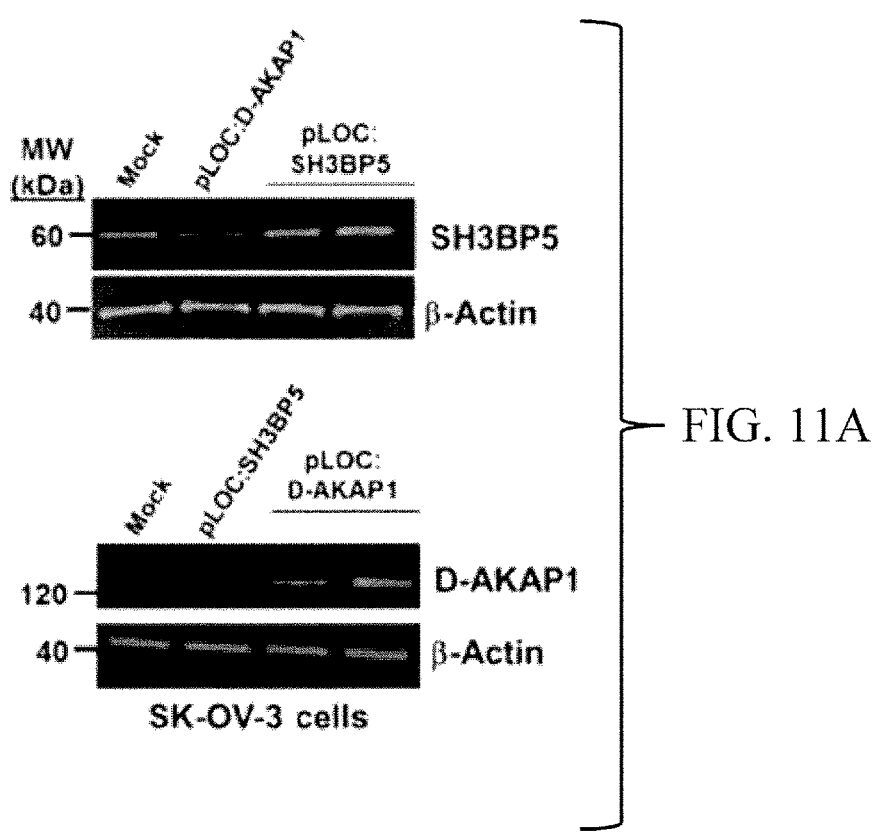
FIGS. 11A-11B show (11A) Over-expression of SH3BP5, but not D-AKAP1, leads to increased cell death (11B) as indicated by SYTOX Green fluorescence.
Figure 11B:
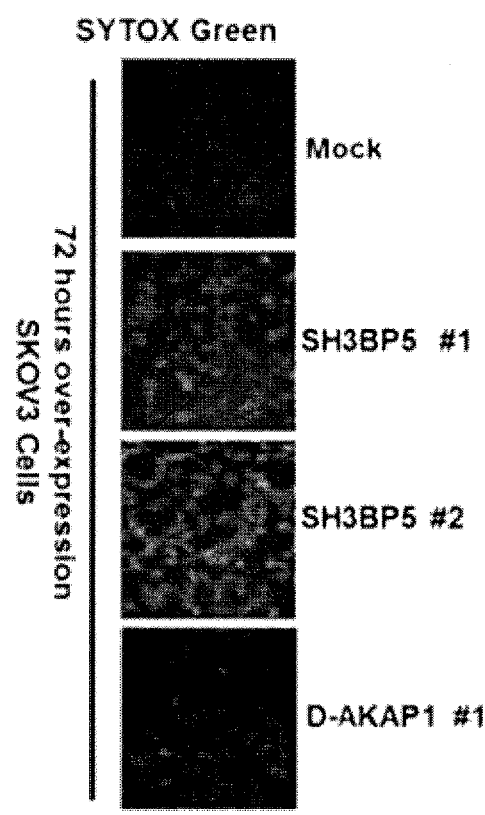

Over-expression of SH3BP5 is toxic to SK-OV-3 ovarian cancer cells. A plasmid over-expressing SH3BP5 (pLOC: SH3BP5) was transfected into SK-OV-3 ovarian cancer cells for 72 hours. Cells were then measured for SH3BP5 over-expression by western blot and viability using SYTOX Green exclusion. As SH3BP5 levels increased (FIG. 11A)

viability of the SK-OV-3 cells decreased as indicated by increased fluorescence of SYTOX Green (FIG. 11B). Meanwhile, cells over-expressing a cyto-protective mitochondrial scaffold, D-AKAP1, (FIG. 11A) or mock transfected cells demonstrated no change in viability (FIG. 11B).

Figure 12A:
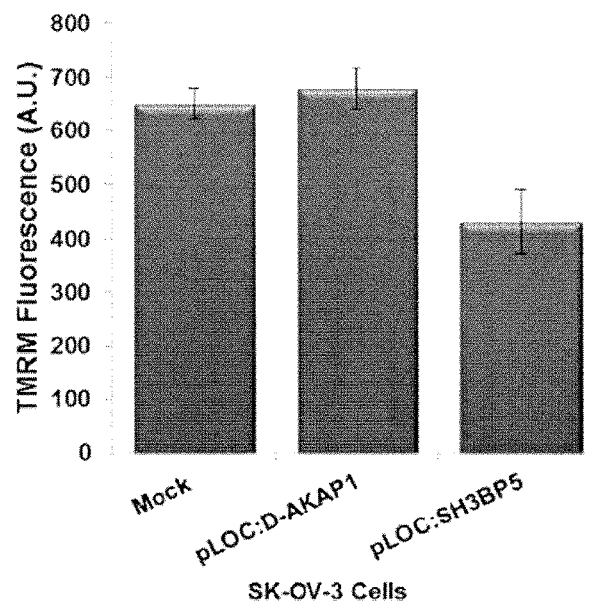
FIGS. 12A-12B show SH3BP5 expression induces loss of mitochondrial membrane potential (12A) and mitochondrial priming (12B).
Figure 12B:
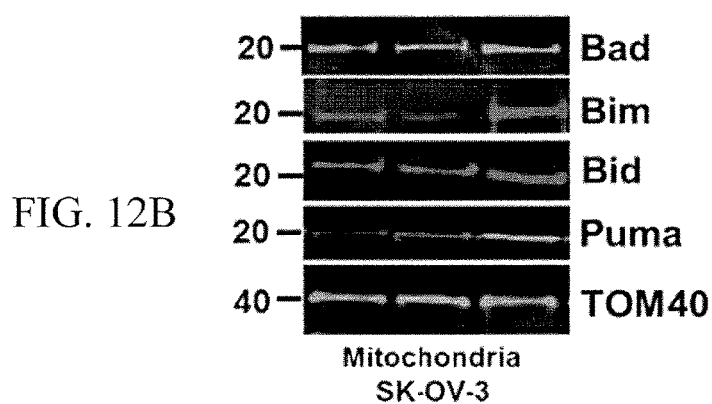

SH3BP5 over-expression primes SK-OV-3 mitochondria for cell death. Mitochondrial membrane potential was determined by staining cells with the potentiometric dye TMRM (tetramethylrhodamine methyl ester) and confocal microscopy. Over-expression of SH3BP5, but not D-AKAP1, was found to decrease mitochondrial membrane potential (FIG. 12A). Furthermore, mitochondria from cells over-expressing SH3BP5 had elevated levels of BH3-only proteins (Bim, Bid, Bad, and Puma) compared to mitochondria from mock transfected and D-AKAP1 over-expressing cells at 48 hours post-transfection (FIG. 12B). We also checked the cells for endoplasmic reticulum stress and induction of the unfolded protein response and these were not elevated in SH3BP5 over-expressing cells (data not shown). This evidence suggests that SH3BP5-mediated signaling primes mitochondria for cell death (FIG. 2).

Figure 13:
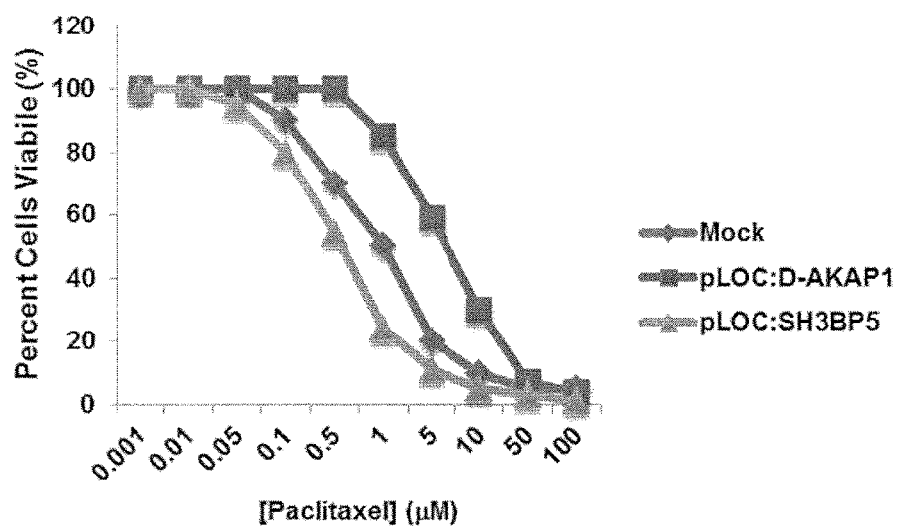
FIG. 13 shows that SH3BP5 expression increases SK-OV-3 cell sensitivity to paclitaxel.

To determine if SH3BP5-induced mitochondrial priming improved SK-OV-3 chemotherapeutic sensitivity, mock transfected, SH3BP5 over-expressing and D-AKAP1 over-expressing cells were treated with increasing doses of paclitaxel following 48 hours of transfection. SH3BP over-expressing cells were 2.5 times more sensitive to paclitaxel treatment compared to mock and D-AKAP1 over-expressing cells (FIG. 13).

As such, an embodiment of the current invention shows that increased levels of SH3BP5 lead to mitochondrial priming and reflect the susceptibility of ovarian cancer to conventional therapy. Accordingly, another embodiment of the current invention provides a novel assay to measure SH3BP5 expression in ovarian cancer cells in a subject and a method of detecting therapeutic sensitivity of the ovarian cancer cells in the subject.

One embodiment of the claimed invention also provides an assay to guide personalized therapeutic selection for ovarian cancer patients, which can be used to prevent unnecessary exposure to toxic drugs.

Another embodiment of the current invention provides an in cell western assay for SH3BP5 along with measures of mitochondrial membrane potential to determine the susceptibility of ovarian cancer cells to chemotherapy. The in-cell western assay (29) to quantitatively measure the levels of SH3BP5 within SK-OV-3 cells is provided. This assay can be used to test an ovarian cancer cell for SH3BP5 expression. Levels of SH3BP5 can be detected using a specific primary antibody and a fluorescent secondary antibody which permits quantitation of the abundance of primary antibody in a well (FIG. 14A) to distinguish SK-OV-03 cells from SK-OV-03 cells that over-express SH3BP5 (FIG. 14C). The signal acquired for SH3BP5 is normalized to the amount of DNA using the dye TO-PRO-3 (Molecular Probes) (FIG. 14B). The Z-prime value for the SH3BP5 assay described herein is 0.72 which indicates high quality of the assay.

Figure 15:
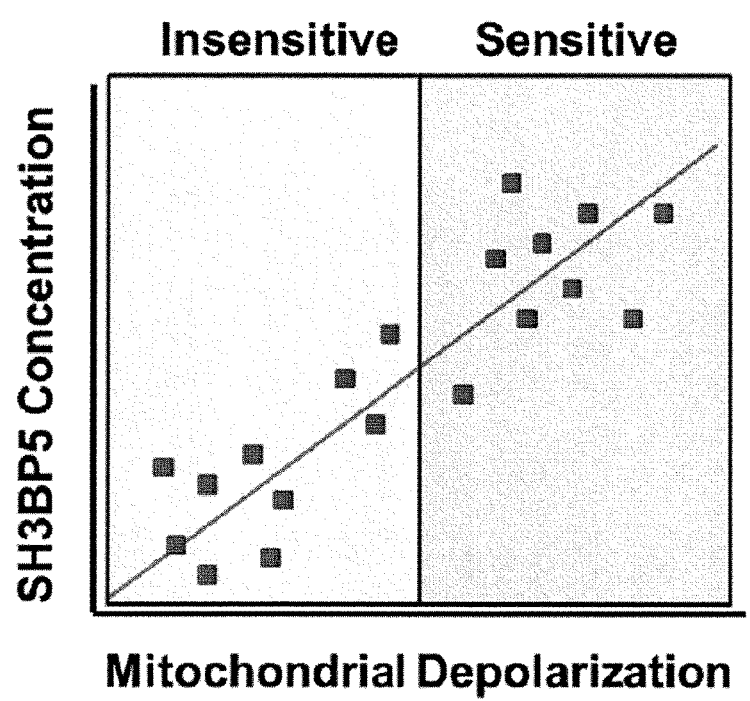
FIG. 15 shows a method for defining ovarian cancers as sensitive or insensitive to chemotherapy.

Because the SH3BP5 in-cell western requires fixation of cells, the mitochondrial membrane potential must be measured before the in cell western assay is performed. Mitochondrial membrane potential can be measured in a high-throughput manner using the potentiometric dye, JC-1. In the presence of depolarizing mitochondria, this dye changes from red fluorescent aggregates to green fluorescent monomers providing quantifiable values. This technique has been used in a high throughput manner to detect mitochondrial priming. A plot of the level of SH3BP5 against the mitochondria depolarization generates an index of mitochondrial priming (FIG. 15). Based on SH3BP5 concentration and mitochondrial membrane potential, a subject suffering from ovarian cancer can be identified as a subject susceptible to chemotherapy or a subject non-responsive to chemotherapy (FIG. 15).

Mitochondrial membrane potential and SH3BP5 expression in 47 ovarian cancer cell lines can be measured with this assay to correlate mitochondrial priming with chemotherapeutic sensitivity. The 47 lines are chosen based on cancer subtypes: Serous (e.g. EF027, OV56), Clear cell (e.g. TOV21G, RMGI), Mucinous (e.g. MCAS, COV644), Endometriod (e.g. OVK18, COV362), Mixed (e.g. IGROV1, 59M), and other (e.g. OC316, SK-OV-3). These cell lines can be subjected to both JC-1 staining and SH3BP5 in-cell western. From these results, population cut-offs can be established (FIG. 15).

Each of the 47 ovarian cancer cell lines can be subjected to a paclitaxel sensitivity analysis (FIG. 13). Cells are grown in increasing concentrations of paclitaxel ranging from 1 nM to 100 µM for 24 hours. Following that time, cellular viability is assessed using a combination of SYTOX Green exclusion dye (FIG. 11B) and resorufin fluorescence. As cells die, retention of SYTOX Green fluorescence increases and resorufin (the oxidized product of resozurin) decreases. Using these two measures, the $IC_{50}$ for paclitaxel of each cell line is determined. To establish the relationship between SH3BP5 expression, mitochondrial priming and chemotherapeutic sensitivity, appropriate statistical analyses is performed. For a linear relationship, the sample correlation coefficient (r) is calculated using linear regression, while the Spearman's rank order correlation coefficient (rs) is determined for non-linear relationships.

Another embodiment of the current invention also provides increasing the effectiveness of cancer treatment, for example, ovarian cancer treatment, by artificially increasing mitochondrial priming. Accordingly, methods of identifying small molecules that increase SH3BP5 expression to improve the effectiveness of existing chemotherapies and to prevent relapse are provided. Accordingly, a further embodiment of the current invention provides methods for identification of agents capable of increasing SH3BP5 expression. The method comprises using the SH3BP5 expression assay, for example, the in cell western assay, to screen small molecule compounds, for example, compounds from chemical libraries, to discover agents that increase SH3BP5 expression in ovarian cancer cells. These screening methods can provide new therapeutic compounds that increase mitochondrial priming and chemotherapeutic efficacy in ovarian cancer. These new agents can serve as chemotherapeutic agents, adjuvant chemotherapies, maintenance therapies between treatments or as chemosensitizers for chemoresistant ovarian cancers.

Agents capable of increasing SH3BP5 levels and mitochondrial priming in ovarian cancer cell lines can be identified using the high-throughput screening assay for SH3BP5 expression as provided herein. The agents to be screened can be obtained from various sources. For example, the small molecule libraries available from the Torrey Pines Institute for Molecular Studies (Port St. Lucie, Fla.) which consist of over 5 million unique small molecules arranged systematically to allow for complete testing with exponentially fewer samples. Another example of the source of the agents to be screened is the library of Food and Drug Administration (FDA) approved drugs that impact mitochondrial function. Currently, 20 such drugs are available, for example, Metformin which is an anti-diabetes drug. Additionally, drugs such as AICAR (N1-(β-D-Ribofuranosyl)-5-aminoimidazole-4-carboxamide) and GW1516 that can mimic the effects of exercise can also be used.

Any ovarian cell line, for example, SK-OV-3 cell line, can be used for the screening assay. The cells are treated with the chemicals for different lengths of time (24 up to 168 hours) following which the cells can be subjected to the in-cell western assay. Potential therapeutic agents fall in two categories: first, cytotoxic agents that elevate SH3BP5 expression and kill SK-OV-3 cells are identified as novel chemotherapeutic agents; and second, chemosensitizers, those compounds that increase SH3BP5 expression and mitochondrial priming but do not kill SK-OV-3 cells, will be identified as adjuvant, maintenance or chemosensitizing therapeutic agents.

To validate that these agents increase SH3BP5 expression in cells, the cell culture and drug treatment can be scaled up so that proteins may be harvested for western blot analysis of SH3BP5. Additionally, selected agents will be monitored for mitochondrial priming by western blot analysis of BH3-only proteins and optionally, by measuring mitochondrial membrane potential. The presence of BH3-only proteins on the mitochondria can be performed by isolating mitochondria from SK-OV-3 cells treated with compound and performing western blots for Bid, Bim, Bad, and Puma (other BH3-only proteins may be included). Mitochondrial membrane potential can be determined in chemically treated cells using confocal microscopy of TMRM fluorescence in mitochondria. Further, cytotoxicity can be verified using a combination of assays to detect apoptosis and these can include TUNEL staining, caspase 3/7 activity assays, and cytochrome c release assays, etc.

By finding compounds capable of reducing cellular tolerance of chemotherapeutic agents, the current invention provides agents that increase the susceptibility of ovarian cancer cells for established therapies. As such, the screening methods of the current invention can be used to identify agents capable of improving treatment, preventing recurrence, and reducing the dose of current chemotherapies.

Example 7—Sub-Chronic Administration of LY294002 Sensitizes Cervical Cancer Cells to Chemotherapy by Enhancing Mitochondrial JNK Signaling A sub-chronic chemo-sensitization model by exposing HeLa cells to low-dose (2 µM) LY294002 was developed. This treatment increased Sab expression on mitochondria, an effect not observed in acute exposures. To examine the role of Sab in chemo-sensitization, Sab was ectopically expressed or silenced in HeLa cells. Elevating Sab levels in HeLa cells increased the efficacy of chemotherapeutic agents, paclitaxel and cisplatin, while silencing Sab decreased the sensitivity of cells towards these agents. The effect of Sab-mediated signaling appeared to be dependent upon mitogen dependent protein kinases (MAPKs) as ablation of Sab's MAPK binding motifs prevented chemo-sensitization. These results suggest that mitochondrial JNK signaling is an adaptable signaling pathway that can be enhanced or restored in cancer cells to improve therapeutic efficacy.

Inhibition of PI3K has been used to reduce cell survival responses and proliferation in human cancers. LY294002, an inhibitor of PI3K signaling, has been used extensively to improve the efficacy of many chemotherapeutics in cell culture. Specifically, LY294002 has been shown to improve the sensitivity of cervical cancer cells to taxols and platinum drugs; two chemotherapies commonly used in clinical settings. However, the doses used in previous studies are high (20-50 µM) when compared to ideal drugs, which have efficacious impacts in the pico- and nano-molar ranges. Thus, dissecting the precise physiological consequences of PI3K inhibition may identify new and more effective targets to improve chemotherapeutic efficacy.

The pro-survival and anti-apoptotic mechanisms of chemoresistance converge on mitochondria, the organelle responsible for regulating metabolism and viability. The invention describes a signaling pathway on the outer mitochondrial membrane that engages mitochondrial dysfunction and cell death. JNK was found to localize to mitochondria in HeLa cells following treatment with anisomycin. This localization and subsequent mitochondrial dysfunction required the protein scaffold Sab (or SH3BP5). Selective inhibition of the JNK-Sab interaction by gene silencing or use of a small cell permeable peptide was sufficient to prevent mitochondrial dysfunction and apoptosis induced by JNK. Mitochondrial JNK signaling is a critical component of early apoptotic signaling in distinct tissues under a variety of stresses.

Scaffold proteins, such as Sab, are essential for organizing signal transduction pathways in the crowded cellular environment. The abundance of particular scaffold proteins can concentrate distinct signal transduction events at precise locations to alter cell physiology. Specifically, enhancing mitochondrial JNK signaling by increasing the concentration of Sab on mitochondria is an effective means to drive cancer cells toward apoptosis. The impact of Sab concentration on the chemo-sensitizing ability of LY294002 in HeLa cell is provided. Increasing Sab expression enhanced the effects of low-dose LY294002 on the efficacy of paclitaxel and cisplatin. Further, silencing Sab prevented LY294002 chemo-sensitization of HeLa cells and reduced cell death in the presence of paclitaxel and cisplatin. Thus, altering outer mitochondrial signaling is an effective strategy for improving chemotherapeutic efficacy.

Sub-Chronic Administration of Low Dose LY294002 Induces Chemo-Sensitization

Figure 16A:
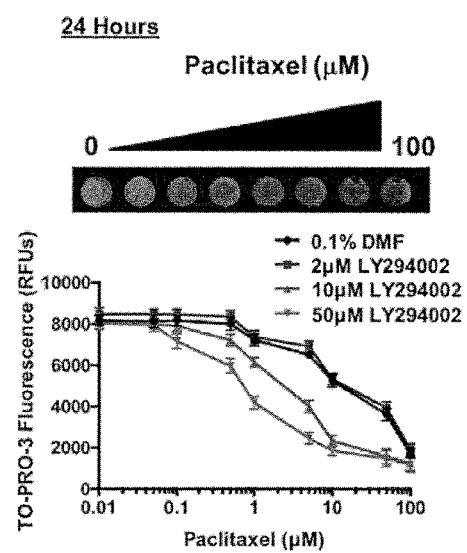
FIGS. 16A-16B show that sub-chronic administration of low dose LY294002 promotes chemo-sensitivity. HeLa cells were treated with 0.1% DMF, 2 µM, 10 µM or 50 µM LY294002 for 24 h (16A) or 7 days (16B). After the indicated amount cells were treated with increasing concentrations of paclitaxel. $IC_{50}$s were then calculated based on TO-PRO-3 staining (tops panels), Fluorescent signals were plotted on GraphPad® Prism.
Figure 16B:
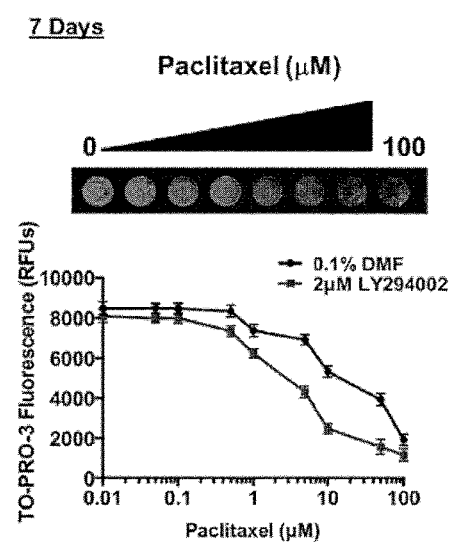

Studies using LY294002 have employed high doses (often >10 µM). To determine if a lower dose of LY294002 could achieve the same effects as high doses, chemosensitivity was examined in HeLa cells treated with acute (24 h) and sub-chronic (7 day) exposures to LY294002. For acute treatments, cells were dosed with 0.1% DMF or increasing concentrations of LY294002 (2 µM, 10 µM, and 50 µM) for 24 h. The $IC_{50}$s for paclitaxel and cisplatin were measured for each dose of LY294002 (FIG. 16A and Table 2). LY294002 improved chemo-sensitivity to both paclitaxel and cisplatin, as cells treated with 50 µM LY294002 had $IC_{50}$s of 1.9 and 0.45 nM, respectively. Meanwhile, 10 µM LY294002 had an $IC_{50}$ of 6.3 µM for paclitaxel and 0.78 nM for cisplatin, and 2 µM LY294002 had a paclitaxel $IC_{50}$ of 14.1 µM and a cisplatin $IC_{50}$ of 2.9 nM, which was similar to untreated and vehicle controls (FIG. 16A and Table 2). The experiment was performed for seven days and while high doses of LY294002 (10 µM and 50 µM) were lethal to HeLa cells, 2 µM LY294002 had little impact on HeLa cell viability. Treatment of HeLa cells with 2 µM LY294002 for 7 days produced $IC_{50}$s for paclitaxel (5.1 µM) and cisplatin (0.54 nM) that were comparable to treatment with 10 µM and 50 µM for 24 h (FIG. 16B and Table 2). These data demonstrate that sub-chronic treatment of low dose LY294002 can induce chemo-sensitivity.

TABLE 2

IC$_{50}$ values for HeLa cells treated with LY294002
or with ectopic expression of Sab.

| | Paclitaxel IC$_{50}$ (μM) | Cisplatin IC$_{50}$ (nM) |
|---|---|---|
| Untreated | 14.7 μM ± 4.1 μM | 3.2 nM ± 1.3 nM |
| Acute (24 h) | | |
| 0.1% DMF | 13.6 μM ± 3.2 μM | 2.7 nM ± 1.1 nM |
| 2 μM LY294002 | 14.1 μM ± 3.2 μM | 2.9 nM ± 1.3 nM |
| 10 μM LY294002 | 6.3 μM ± 4.8 μM | 0.78 nM ± 0.4 nM |
| 50 μM LY294002 | 1.9 μM ± 1.1 μM | 0.45 nM ± 0.4 nM |
| Sub-chronic (7 days) | | |
| 0.1% DMF | 13.9 μM ± 2.6 μM | 2.9 nM ± 1.4 nM |
| 2 μM LY294002 | 5.1 μM ± 3.9 μM | 0.54 nM ± 0.3 nM |
| Ectopic expression | | |
| RFP | 13.4 μM ± 3.5 μM | 2.9 nM ± 1.0 nM |
| Sab | 4.7 μM ± 2.8 μM | 0.42 nM ± 0.3 nM |
| Sab: KIM1/2-L/A | 13.8 μM ± 3.3 μM | 3.1 nM ± 1.4 nM |
| Gene silencing | | |
| Control shRNA | 15.3 μM ± 3.5 μM | 3.9 nM ± 1.0 nM |
| Sab shRNA#1 | 61.8 μM ± 7.1 μM | 12.1 nM ± 1.9 nM |
| Sab shRNA#2 | 73.4 μM ± 9.3 μM | 18.8 nM ± 3.2 nM |
| Sab shRNA#2 + Sab: shRNA$^r$ | 28.0 μM ± 12.8 μM | 7.3 nM ± 4.4 nM |

±: represents the relative standard deviation from the mean.

Sub-Chronic LY294002 Increases Sab Expression and Mitochondrial JNK Signaling

Figure 17A:
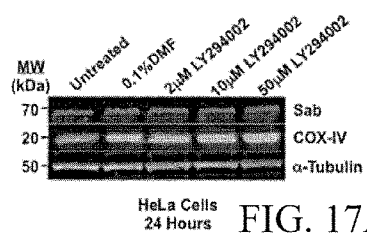
FIGS. 17A-17D show that sub-chronic, but not acute, LY294002 treatment increases mitochondrial JNK signaling. (17A) HeLa cells were exposed to 0.1% DMF, 2 µM, 10 µM or 50 µM LY294002 for 24 h, and cells were lysed and examined for Sab expression. (17B) HeLa cells were treated with 0.1% DMF, 2 µM, 10 µM or 50 µM LY294002 for 7 days, and cells were lysed daily and examined for levels of Sab, phosphorylated (active) JNK, and total JNK, (17C) Mitochondria were isolated from HeLa cells treated with either DMF or 2 µM LY294002. Isolated mitochondria were lysed and examined for MAPK signaling proteins and sub-cellular contaminants. (17D) WT and JNK knockout MEFs were analyzed for Sab expression by western blot (top). Western blots were quantified using the LI-COR Odyssey CLx imager.
Figure 17B:
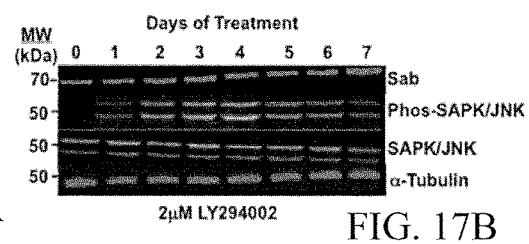
Figure 17C:
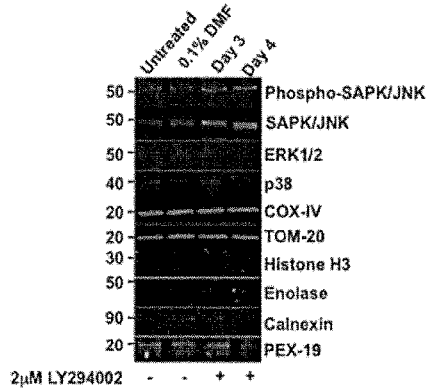
Figure 17D:
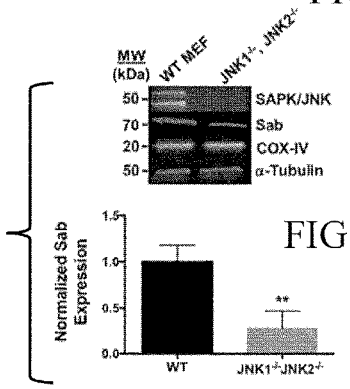
Figure 18A:
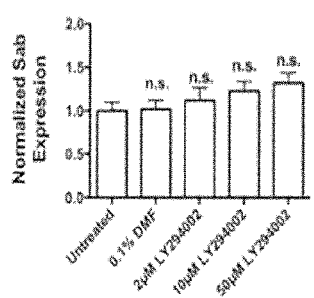
FIGS. 18A-18C show quantitation of Western Blot Analysis for FIGS. 17A-17D. For the experiments described in FIGS. 17A-17D, fluorescence signals from proteins of interest were divided by the signals from loading controls. Mitochondrial proteins, such as Sab, were divided by the fluorescence signal for COX-IV, and cellular protein fluorescence was divided by the fluorescence of α-tubulin. Individual samples were then normalized to untreated controls. Western blot quantification was performed for (18A) Sab expression in acute treated HeLa cells. (18B) Sub-chronic administration of LY294002, and (18C) Phospho-JNK levels during sub-chronic exposure to LY294002. The K-value for all western blot images was set at 0 for each experiment.
Figure 18B:
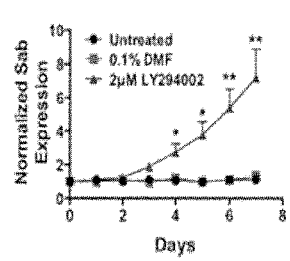
Figure 18C:
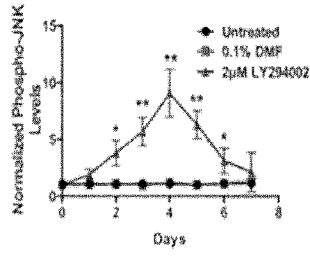

To determine if LY294002 impacted the concentration of JNK signaling on mitochondria, the expression of Sab was measured in HeLa cells in both acute and sub-chronic administration of LY294002. HeLa cells were treated with 2 μM, 10 μM and 50 μM LY294002 over 24 h, and neither condition increased Sab expression above that of 0.1% DMF and untreated controls (FIG. 17A, quantified in FIG. 18A). To ascertain if prospective changes in Sab levels were due to a change in mitochondrial number, COX-IV was employed as a mitochondrial loading control, and FIG. 17A demonstrates equivalent mitochondrial amounts were present. α-tubulin was employed as a cellular loading control (FIG. 17A). To determine if Sab expression changed during subchronic treatment with 2 μM LY294002, HeLa cells were treated with 2 μM LY294002 or DMF for 7 days. As time increased, there was a noticeable increase (~8-fold) in Sab expression in the LY294002 compared to DMF-treated and untreated cells (FIG. 17B and quantified in FIG. 18B). Since Sab expression increased during LY294002 treatment, we examined JNK activation (phosphorylation) during the time course as well (FIG. 17B). Analysis of the protein lysates from our time-course experiment revealed that phospho-JNK levels increased (over 10-fold) between days 2 and 4 before diminishing after day 4 (FIG. 17B and quantified FIG. 18C). No changes were noted in the level of total JNK (FIG. 17B). To determine if mitochondrial translocation of JNK occurred during the sub-chronic treatment, mitochondrial isolates were analyzed for the presence of JNK on days 3 and 4 (the days of maximal JNK activation). Analysis of the LY294002 exposure revealed that JNK levels increased on mitochondria between days 3 and 4 (FIG. 17C). Moreover, the JNK migrating to mitochondria was active JNK (Phospho-JNK) (FIG. 17C). ERK1/2 or p38 were not observed in the mitochondria isolated at the selected times of the LY294002 time course (FIG. 17C). The mitochondrial preparations (COX-IV and TOM20) were shown to have low contamination from nuclear (histone H3), cytosolic (enolase), and microsomal fractions (calcineurin) (FIG. 17C). Some contamination was observed from the peroxisomes (PEX19) (FIG. 17C). To determine if JNK could be propagating its own mitochondrial signaling, Sab levels were examined in WT and JNK1$^{-/-}$/JNK2$^{-/-}$ MEFs. Compared to WT MEFs, JNK1$^{-/-}$/JNK2$^{-/-}$ MEFs had markedly decreased Sab expression (3-4 fold on average) (FIG. 17D). These data suggest that low-grade induction of JNK signaling may be sufficient to promote mitochondrial JNK signaling during chemo-sensitization.

Increasing Sab Expression Confers Chemo-Sensitivity in HeLa Cells

Figure 19A:
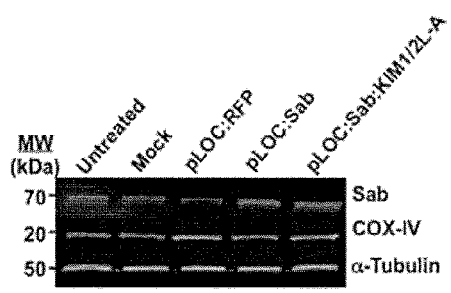
FIGS. 19A-19F shows that over-expression of Sab promotes chemo-sensitivity, while silencing Sab enhances chemo-resistance. (19A) HeLa cells were transfected (or mock transfected) with plasmids expressing RFP, Sab, or a MAPK-binding deficient mutant (Sab:KIM1/2L-A). Sab expression was monitored by western blot analysis after 72 h. (19B) $IC_{50}$s were then calculated for paclitaxel and cisplatin. (19C) HeLa cells were transfected with plasmids expressing shRNAs designed to silence Sab. Sab expression was assessed by western blot analysis after 72 h of transfection. (19D) $IC_{50}$s again were calculated for paclitaxel and cisplatin. (19E) An shRNA-resistant mutant (Sab:shRNAr) was expressed in HeLa cells to rescue Sab-mediated chemosensitization. Cells were transfected 72 h prior to western blot analysis. (19F) $IC_{50}$s were calculated using TO-PRO-3 staining.
Figure 19B:
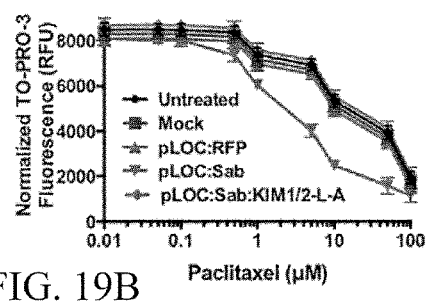
Figure 19C:
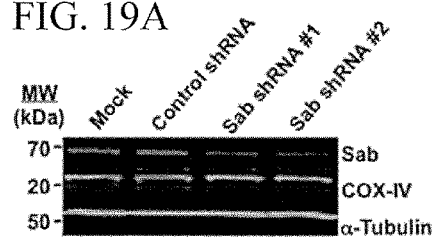
Figure 19D:
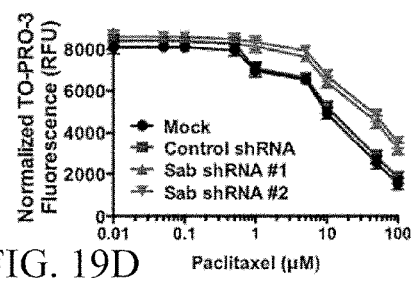
Figure 19E:
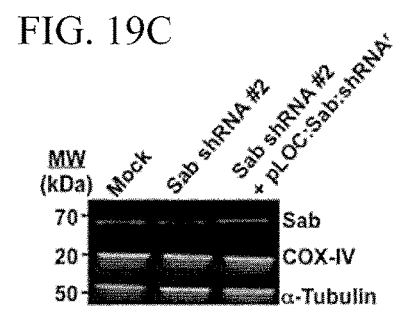

To determine if the chemo-sensitivity induced by subchronic, low dose LY294002 was dependent upon the level of mitochondrial JNK signaling, chemo-sensitivity was examined in HeLa cells ectopically expressing or silencing Sab. First, HeLa cells were transiently transfected with either pLOC:RFP or pLOC:Sab (FIG. 19A) for 48 h and then treated the cells with increasing concentrations of paclitaxel or cisplatin for 24 h. Increasing Sab expression resulted in a 5-fold decrease in the IC$_{50}$ of paclitaxel in HeLa cells when compared to untreated or mock-transfected cells and HeLa cells expressing RFP (FIG. 19B and Table 2). To determine if this sensitization was directly due to the interaction between JNK and Sab, the KIM motifs of Sab were mutated to prevent JNK binding (pLOC:Sab:KIM1/2-L-A). Ectopic expression of this JNK binding deficient version of Sab had no impact on the IC$_{50}$s for paclitaxel or cisplatin in HeLa cells (FIG. 19B and Table 2). To further validate the role of Sab in chemo-sensitivity, cells were treated with either a control shRNA or Sab-specific shRNAs for 72 h (FIG. 19C) and then exposed to increasing doses of paclitaxel or cisplatin. Silencing Sab increased the IC$_{50}$s for both paclitaxel and cisplatin when compared to mock-transfected and control shRNA treated cells (FIG. 19D and Table 2). To determine if the knockdown of Sab was indeed responsible for the chemo-resistance observed in the previous experiment, an shRNA-resistant mutant of Sab (pLOC:Sab:shRNA$^r$) was expressed for 72 h (FIG. 19E), and repeated the IC$_{50}$ measurements for both paclitaxel and cisplatin.

Figure 19F:
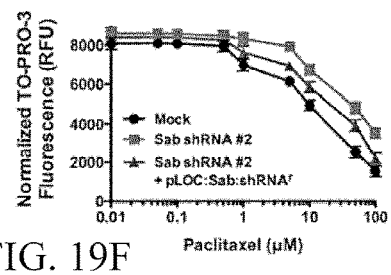

FIG. 19F demonstrates that recovery of Sab expression yields IC$_{50}$s of 28 μM and 7.3 nM for paclitaxel and cisplatin, respectively (Table 2). These data demonstrate that the extent of mitochondrial JNK signaling may be a significant determinant for chemo-responsiveness of cancer cells.

Chemo-resistance is typified by altered mitochondrial physiology that culminates in the inhibition of cell death. The ability to restore apoptosis in resistant cancer cells hinges on the ability to re-establish death signaling to mitochondria and this can be accomplished by increasing mitochondrial JNK signaling in cancer cells. To examine how PI3K inhibition may impact cancer cell physiology over a chemotherapy regimen, a sub-chronic low dose treatment of LY294002 (2 μM) was employed over the course of a week. This approach yielded the same impact on chemotherapeutic efficacy as acute doses of 10 μM and 50 μM LY294002.

The absence of these large doses permitted examination of the cellular changes that may occur during chemo-sensitization. Sab expression increased during chemo-sensitization; further, mitochondrial JNK levels were elevated during the sub-chronic model (FIG. 19C).

Low dose sub-chronic cellular stress can lead to an increase in Sab expression which suggests that Sab expression can be modulated by the cellular environment which influences mitochondrial physiology, for example, apoptosis. This pathway could be enhanced or inhibited to drive apoptotic responses in cells or tissues affected by diseases.

JNK was required for mitochondrial JNK signaling, and ablation of the JNK binding sites on Sab reduced the efficacy of chemotherapeutic agents (FIG. 19, Table 2). In contrast, silencing Sab expression did not enhance chemo-sensitization, but in fact promoted chemo-resistance. Sab expression is decreased in late stage and resistant cancers at the mRNA level which suggests that inhibition of mitochondrial JNK signaling may be a mechanism by which gynecological cancers become resistant to chemotherapy and other treatments. Restoring mitochondrial JNK signaling in chemically resistance gynecological cancers provides a useful approach to recover chemo-sensitivity.

Mitochondrial JNK is necessary for sub-chronic chemo-sensitization by LY294002; however, JNK was partly responsible for Sab expression (FIG. 17). Therefore, under physiological and certain stress conditions, JNK signaling amplifies mitochondrial dysfunction by inducing Sab expression. As such, JNK creates a positive feedback loop and enhances Sab-mediated events on mitochondria. Mitochondrial JNK signaling amplifies mitochondrial reactive oxygen species generation and inhibits anti-apoptotic functions of Bcl-2 leading to mitochondrial depolarization. The production of oxidants and loss of mitochondrial membrane potential have been shown to activate JNK signaling. Thus, nuclear JNK can increase Sab-mediated signaling leading to mitochondrial toxicity. As such, therapies that enhance mitochondrial JNK signaling by increasing Sab expression can be effective in sustaining cell death in cancer cells.

A potential side-effect of increasing Sab expression may be elevated toxicity in non-cancerous tissues. Thus, selectively targeting substances capable of inducing Sab expression to cancer cells would be the preferred approach to enhance early apoptotic responses.

The invention provides an inducible mechanism to exacerbate apoptotic responses. Also, enhancing mitochondrial JNK signaling is a viable approach to recover apoptotic capacity in chemo-resistant cancer cells. Combination chemotherapeutic regimens that couple chemo-sensitizing agents and enhanced mitochondrial JNK signaling may be useful strategies to lower the dose of toxic chemotherapeutic agents and improve treatment outcomes in cancer.

REFERENCES

1. Jemal A, Siegel R, Ward E, Hao Y, Xu J, et al. 2008. *CA Cancer J Clin* 58: 71-96
2. Parkin D M, Bray F, Ferlay J, Pisani P. 2005. *CA Cancer J Clin* 55: 74-108
3. Yap T A, Carden C P, Kaye S B. 2009. *Nat Rev Cancer* 9: 167-81
4. Chen G, Wang F, Trachootham D, Huang P. 2010. *Mitochondrion* 10: 614-25
5. Letai A G. 2008. *Nat Rev Cancer* 8: 121-32
6. Reed J C. 2011. *Science* 334: 1075-6
7. Letai A, Bassik M C, Walensky L D, Sorcinelli M D, Weiler S, Korsmeyer S J. 2002. *Cancer Cell* 2: 183-92
8. Davids M S, Deng J, Wiestner A, Lannutti B J, Wang L, et al. 2012. *Blood* 120: 3501-9
9. Ni Chonghaile T, Sarosiek K A, Vo T T, Ryan J A, Tammareddi A, et al. 2011. *Science* 334: 1129-33
10. Nieminen A I, Partanen J I, Hau A, Klefstrom J. 2007. *EMBO J* 26: 1055-67
11. Kim M-J, Lee K-H, Lee S-J. 2008. *FEBS Journal* 275: 2096-108
12. Sharma H, Sen S, Singh N. 2005. *Cancer Biology & Therapy* 4: 949-55
13. Ito Y, Mishra N C, Yoshida K, Kharbanda S, Saxena S, Kufe D. 2001. *Cell Death Differ* 8: 794-800
14, Kang Y H, Lee S J. 2008. *J Cell Physiol* 217: 23-33
15. Chambers J W, Cherry L, Laughlin J D, Figuera-Losada M, Lograsso P V. 2011. *ACS Chem Biol* 6: 808-18
16. Wiltshire C, Gillespie D A, May G H. 2004. *Biochem Soc Trans* 32: 1075-7
17. Wiltshire C, Matsushita M, Tsukada S, Gillespie D A, May G H. 2002. *Biochem J* 367: 577-85
18. Chambers J W, LoGrasso P V. 2011. *J Biol Chem* 286: 16052-62
19. Court N W, Kuo I, Quigley O, Bogoyevitch M A. 2004. *Biochem Biophys Res Commun* 319: 130-7
20. Yamadori T, Baba Y, Matsushita M, Hashimoto S, Kurosaki M, et al. 1999. *Proc Natl Acad Sci USA* 96: 6341-6
21. Matsushita M, Yamadori T, Kato S, Takemoto Y, Inazawa J, et al. 1998. *Biochem Biophys Res Commun* 245: 337-43
22. Rosenzweig K E, Youmell M B, Palayoor S T, Price B D. 1997. *Clinical Cancer Research* 3: 1149-56
23. Irminger-Finger I, Soriano J V, Vaudan G, Montesano R, Sappino A-P. 1998. *The Journal of Cell Biology* 143: 1329-39
24. Certo M, Del Gaizo Moore V, Nishino M, Wei G, Korsmeyer S, et al. 2006. *Cancer Cell* 9: 351-65
25. Goldsmith K C, Gross M, Peirce S, Luyindula D, Liu X, et al. 2012. *Cancer Res* 72: 2565-77
26. Vo T T, Ryan J, Carrasco R, Neuberg D, Rossi D J, et al. 2012. *Cell* 151: 344-55
27, Ward M W, Huber H J, Weisova P, Dussmann H, Nicholls D G, Prehn J H. 2007, *J Neurosci* 27: 8238-49
28. Ward M W, Rego A C, Frenguelli B G, Nicholls D G. 2000. *J Neurosci* 20: 7208-19
29. Wong S K F. 2004. *Analytical Biochemistry* 333: 265-72
30. Smiley S T, Reers M, Mottola-Hartshorn C, Lin M, Chen A, et al. 1991. *Proceedings of the National Academy of Sciences* 88: 3671-5
31. Ryan J A, Brunelle J K, Letai A. 2010. *Proc Natl Acad Sci USA* 107: 12895-900
32. Domcke S, Sinha R, Levine D A, Sander C, Schultz N. 2013. *Nat Commun* 4: 2126
33. Wu J, Zhang Y, Maida L E, Santos R G, Welmaker G S, et al. 2013. *J Med Chem*
34. Owen M R, Doran E, Halestrap A P. 2000. *Biochem J* 348 Pt 3: 607-14
35. Narkar V A, Downes M, Yu R T, Embler E, Wang Y-X, et al. 2008. *Cell* 134: 405-15
36. Chambers J W, Howard S, LoGrasso P V. 2013. *J Biol Chem* 288: 1079-87
37. Chambers J W, Pachori A, Howard S, Iqbal S, LoGrasso P V. 2013. *J Biol Chem* 288: 4000-11

We claim:

1. A method of assessing susceptibility of a cancer in a subject to a chemotherapeutic treatment selected from docetaxel, paclitaxel, 6-mercaptopurine, cisplatin, vorinostat, romidepsin, and pralatrexate and treating the subject with the chemotherapeutic treatment for the cancer, the method comprising the steps of:
   a) isolating mitochondria from a biological sample comprising cancer cells obtained from the subject and a control sample comprising non-cancer cells;
   b) detecting the levels of Src homology 3 domain binding protein 5 (SAB protein), Bcl-2 protein, and Bim protein in the isolated mitochondria;
   c) identifying the subject as being susceptible to the chemotherapeutic treatment if the mitochondria of the cancer cells of the biological sample obtained from the subject have an increased level of SAB protein, an increased level of Bim protein and a decreased level of Bcl-2 protein relative to the levels of SAB protein, Bim protein, and Bcl-2 protein in the mitochondria of the non-cancer cells of the control sample; and
   d) administering the chemotherapeutic treatment for the cancer to the subject identified as being susceptible to the chemotherapeutic treatment.

2. The method of claim 1, wherein the cancer is selected from leukemia, bladder cancer, bone cancer, brain tumor, central nervous system tumors, brain and spinal cord tumors, breast cancer, bronchial tumors, Burkitt lymphoma, gastrointestinal cancer, cervical cancer, colorectal cancer, esophageal cancer, head and neck cancer, liver cancer, Hodgkin lymphoma, islet cell tumors, Kaposi sarcoma, kidney cancer, laryngeal cancer, lip and oral cavity cancer, lung cancer, non-small cell lung cancer, small cell lymphoma, AIDS-related lymphoma, Burkitt lymphoma, cutaneous T-cell lymphoma, non-Hodgkin lymphoma, ovarian cancer, testicular cancer, and vaginal cancer.

3. The method of claim 1, wherein the biological sample comprising cancer cells is a tissue sample, aqueous humour, vitreous humour, bile, blood, cerebrospinal fluid, endolymph, perilymph, exudates, lymph, mucus, pericardial fluid, pleural fluid, or synovial fluid.

4. The method of claim 1, wherein the step of detecting the level of SAB protein comprises using an antibody that specifically binds to SAB protein.

5. The method of claim 4, wherein the antibody comprises a label selected from a fluorescent molecule, radioactive molecule, enzyme, chromogenic substrate, and fluorogenic substrate.

6. The method of claim 4, wherein the antibody is bound by a second binding antibody.

7. The method of claim 6, wherein the second binding antibody comprises a label selected from a fluorescent molecule, radioactive molecule, enzyme, chromogenic substrate, and fluorogenic substrate.

8. The method of claim 4, wherein the step of detecting the level of SAB protein comprises performing immunoblotting, immunoprecipitation, immunofluorescence, immunostaining, immunoelectrophoresis, enzyme-linked immunosorbent assay (ELISA), or in-cell western blotting.

9. The method of claim 1, wherein the method further comprises detecting the level of COX-IV protein in the isolated mitochondria; wherein the level of COX-IV protein is detected using an antibody that specifically binds to COX-IV protein.

10. The method of claim 9, wherein the step of detecting the level of SAB protein comprises using an antibody that specifically binds to SAB protein, wherein the antibody that specifically binds to SAB protein is an antibody comprising a label that is a fluorescent molecule and the antibody that specifically binds to COX-IV protein is an antibody comprising a label that is a fluorescent molecule.

11. The method of claim 10, wherein the step of identifying the subject as being susceptible to the chemotherapeutic treatment comprises detecting the fluorescent signal intensity for SAB protein and COX-IV protein in the isolated mitochondria and dividing the fluorescent signal intensity for SAB protein by the fluorescent signal intensity for COX-IV protein and further dividing the quotient of SAB fluorescent signal intensity and COX-IV fluorescent signal intensity from the isolated mitochondria of the biological sample by the quotient of SAB fluorescent signal intensity and COX-IV fluorescent signal intensity from the isolated mitochondria of the control sample.

12. The method of claim 1, further comprising quantifying the protein levels of Bcl-XL, Bid, Bad, Puma, Bax and/or Bak in the isolated mitochondria.

13. The method of claim 12, wherein the subject is identified as being susceptible to the chemotherapeutic treatment if the isolated mitochondria of the cancer cells of the biological sample obtained from the subject have decreased protein levels of the Bax or Bak compared to the isolated mitochondria of non-cancer cells of the control sample.

14. The method of claim 1, further comprising determining mitochondrial function in the cancer cells and the non-cancer cells.

15. The method of claim 14, wherein the step of determining mitochondrial function comprises measuring a mitochondrial membrane potential using JC-1 dye or Tetramethylrhodamine (TMRM).

16. The method of claim 14, wherein the step of determining mitochondrial function comprises measuring oxygen consumption rate, fluorescently-labeled glucose uptake, or superoxide generation.

\* \* \* \* \*

SEQUENCE LISTING

<160> NUMBER OF SEQ ID NOS: 7

<210> SEQ ID NO 1
<211> LENGTH: 38
<212> TYPE: DNA
<213> ORGANISM: Artificial Sequence
<220> FEATURE:
<223> OTHER INFORMATION: Sense oligonucleotide for KIM1 mutagenesis.

<400> SEQUENCE: 1
gtgaggcctg gcagcgcgga tgcgcccagc cctgtgtc                               38

<210> SEQ ID NO 2
<211> LENGTH: 38
<212> TYPE: DNA
<213> ORGANISM: Artificial Sequence
<220> FEATURE:
<223> OTHER INFORMATION: Anti-sense oligonucleotide for KIM1
      mutagenesis.

<400> SEQUENCE: 2
gacacagggc tgggcgcatc cgcgctgcca ggcctcac                               38

<210> SEQ ID NO 3
<211> LENGTH: 44
<212> TYPE: DNA
<213> ORGANISM: Artificial Sequence
<220> FEATURE:
<223> OTHER INFORMATION: Sense oligonucleotide for KIM2 mutagenesis.

<400> SEQUENCE: 3
gagaaccgga tgaagcaggc ctccgcacag tgctcaaagg gaag                        44

<210> SEQ ID NO 4
<211> LENGTH: 38
<212> TYPE: DNA
<213> ORGANISM: Artificial Sequence
<220> FEATURE:
<223> OTHER INFORMATION: Anti-sense oligonucleotide for KIM2
      mutagenesis.

<400> SEQUENCE: 4
gacacagggc tgggcgcatc cgcgctgcca ggcctcac                               38

<210> SEQ ID NO 5
<211> LENGTH: 19
<212> TYPE: DNA
<213> ORGANISM: Artificial Sequence
<220> FEATURE:
<223> OTHER INFORMATION: shRNA to inhibit Sab expression.

<400> SEQUENCE: 5
cctgtcagag tttgggatg                                                    19

<210> SEQ ID NO 6
<211> LENGTH: 19
<212> TYPE: DNA
<213> ORGANISM: Artificial Sequence
<220> FEATURE:
<223> OTHER INFORMATION: Sense oligonucleotide for introducing silent
      mutations in Sab expression constructs.

<400> SEQUENCE: 6
tgtgtccctt tcggaattt                                                    19

<210> SEQ ID NO 7

```
<211> LENGTH: 20
<212> TYPE: DNA
<213> ORGANISM: Artificial Sequence
<220> FEATURE:
<223> OTHER INFORMATION: Anti-sense oligonucleotide for introducing
      silent mutations in Sab expression constructs.

<400> SEQUENCE: 7
aacactggga acatcatccc                                                   20
```